United States Patent [19]

Ward

[11] Patent Number: 4,568,376
[45] Date of Patent: Feb. 4, 1986

[54] HERBICIDAL 5-AMINO-3-OXO-4-(SUBSTITUTED-PHENYL)-2,3-DIHYDROFURAN AND DERIVATIVES THEREOF

[75] Inventor: Carl E. Ward, San Jose, Calif.

[73] Assignee: Chevron Research Company, San Francisco, Calif.

[21] Appl. No.: 723,768

[22] Filed: Apr. 16, 1985

Related U.S. Application Data

[63] Continuation-in-part of Ser. No. 607,610, May 8, 1984, abandoned, which is a continuation-in-part of Ser. No. 505,169, Jun. 17, 1983, abandoned.

[51] Int. Cl.$^4$ .................... A01N 43/08; C07D 307/52
[52] U.S. Cl. .......................................... 71/88; 71/94; 71/95; 260/239 A; 546/214; 546/283; 548/517; 549/479
[58] Field of Search ............... 549/479; 260/239 A; 546/214, 283; 548/517; 71/88, 94, 95

[56] References Cited

U.S. PATENT DOCUMENTS 4,441,910  4/1984  Shapiro ................................. 71/90

FOREIGN PATENT DOCUMENTS 42-19090  9/1967  Japan .
44-13710  6/1969  Japan .
1521092   8/1978  United Kingdom .
2080289   2/1982  United Kingdom .

OTHER PUBLICATIONS

Capraro et al, Helvetica Chimica Acta–vol. 66, Fasc. 1 (1983)–No. 31, pp. 362–378.
Umio, et al, Chem. Abstracts, vol. 70, 1969, 68123t.
Volovenko et al; Chem. Abstracts, vol. 95, 1981, 24799e.
Meier et al, Chemical Abstracts, vol. 94 (1981), 138818v.

Primary Examiner—Richard L. Raymond
Attorney, Agent, or Firm—T. G. DeJonghe; L. S. Squires

[57] ABSTRACT

5-Amino-3-oxo-4-(substituted-phenyl)-2,3-dihydrofuran and derivatives thereof. The compounds generally exhibit both pre-emergence and post-emergence phytotoxicity and are useful as herbicides and also at low dosages as plant growth regulating agents.

47 Claims, No Drawings

HERBICIDAL 5-AMINO-3-OXO-4-(SUBSTITUTED-PHENYL)-2,3-DIHYDROFURAN AND DERIVATIVES THEREOF

CROSS-REFERENCE TO RELATED APPLICATIONS

This application is a continuation-in-part of U.S. application Ser. No. 607,610, filed May 8, 1984, and now abandoned, which in turn is a continuation-in-part of U.S. application Ser. No. 505,169, filed June 17, 1983, and now abandoned.

BACKGROUND OF THE INVENTION

This invention relates to 5-amino-3-oxo-4-(substituted-phenyl)-2,3-dihydrofuran derivatives and to the use of such compounds as herbicides and plant growth regulators.

Chemiker-Zeitung 104 (1980) No. 10, Pages 302–303, is an academic paper disclosing the ring closure of 1-(dimethylamino)-2,4-diphenyl-1-buten-3,4-dione to yield 5-dimethylamino-2,4-diphenyl-2,3-dihydrofuran. British Pat. No. 1,521,092, discloses certain 3-phenyl-5-substituted-4(1H)-pyrid-ones or -thiones as herbicides. Japanese Patent Application 13,710/69 (Chemical Abstracts 71:61195e) discloses the generic formula for 5-amino-3-oxo-4-(phenyl and halophenyl)-2,3-dihydrofuran and specifically discloses 5-amino-3-oxo-4-(phenyl and 4-chlorophenyl)-2,3-dihydrofurans. Japanese Patent No. 19090 (Chemical Abstracts 69P10352e) discloses certain 2,3-dihydrothiophenes as pharmaceuticals. *Helvetica Chemica Acta*, Volume 66, Pages 362–378 (1983) discloses 5-N-cyclopropyl-4-phenyl-2-methoxycarbonylmethylene-3-furanone as part of an academic chemical synthesis discussion. U.S. Pat. No. 4,441,910 discloses herbicidal ureidosulfonylfurans and ureidosulfonylthiophenes.

SUMMARY OF THE INVENTION

The present invention provides compounds having both pre-emergence and post-emergence herbicidal activity and having especially good pre-emergence activity against a broad spectrum of both broad-leaf weeds and grassy weeds. At lower application rates the compounds also exhibit plant growth regulating properties.

The compounds of the present invention can be represented by the following formula:

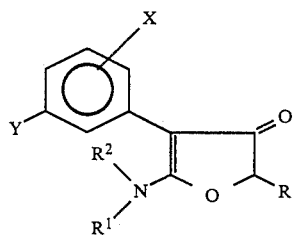
(I)

wherein R is lower alkyl having 1 through 4 carbon atoms; cycloalkyl having 3 through 7 carbon atoms, lower alkenyl; haloalkyl having 1 through 4 carbon atoms and 1 through 3 halo atoms independently selected from the group of fluoro, chloro, bromo or iodo; haloalkenyl having 2 through 4 carbon atoms and 1 through 3 halo atoms independently selected from the group of fluoro, chloro, bromo, or iodo; lower alkoxyalkyl wherein the alkoxy and alkyl moiety thereof independently have 1 through 3 carbon atoms; lower alkylthioalkyl wherein the alkyl moieties independently have 1 through 3 carbon atoms; phenyl, naphth-1-yl, inden-1-yl; 4-fluorophenyl; arylalkylene having 1 through 3 carbon atoms in the alkylene moiety and wherein said aryl moiety is phenyl, naphth-1-yl or inden-1-yl; or substituted aryl or arylalkylene selected from the group having the formulas:

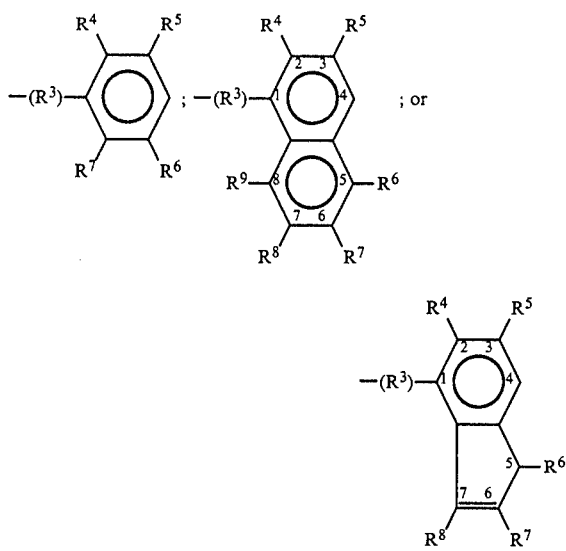

wherein one, two or three of $R^4$, $R^5$, $R^6$, $R^7$, $R^8$, and $R^9$ are independently selected from the group of lower alkyl, lower alkoxy, halo, nitro, or haloalkyl having 1 through 3 carbon atoms and 1 through 3 of the same or different halo atoms, and the remainder are hydrogen; and $R^3$ is a single bond or an alkylene having 1 through 3 carbon atoms;

$R^1$ is hydrogen or alkyl having 1 through 4 carbon atoms;

$R^2$ is hydrogen, alkyl having 1 through 4 carbon atoms, alkenyl having 3 or 4 carbon atoms, alkoxycarbonylalkyl having from 1 through 4 carbon atoms in the alkoxy moiety and from 1 through 4 carbon atoms in the alkyl moiety alkoxyalkyl wherein the alkoxy and alkyl moieties independently have 1 through 3 carbon atoms or alkylthioalkyl wherein the alkyl moieties independently have 1 through 3 carbon atoms; or $R^1$ and $R^2$ together with the nitrogen to which they are joined form a saturated or unsaturated nitrogen heterocycle having from 4 through 6 ring atoms one of which is nitrogen and the remainder of which are carbon atoms;

X is hydrogen, lower alkyl, lower alkoxy, halo, or trifluoromethyl and can be at any available position on the phenyl ring; and Y is lower alkyl, lower alkoxy; halo; lower haloalkyl having 1 through 4 carbon atoms and 1 to 3 of the same or different halo atoms; lower haloalkoxy having 1 through 4 carbon atoms and 1 through 3 of the same or different halo atoms; or lower haloalkylthio having 1 through 4 carbon atoms and 1 through 3 of the same or different halo atoms; with the proviso that when Y is halo then R, $R^1$ and $R^2$ are not all hydrogen and the further proviso that when Y is other than trifluoromethyl and X is other than hydrogen, and $R^1$ is hydrogen and $R^2$ is hydrogen then R is methyl, ethyl, propyl, 2-halophenyl, 2-lower alkylphenyl or 4-fluorophenyl.

The invention also comprises compatible salts of the compound of Formula (I), for example, acid addition salts with respect to the exocyclic amino group; and also salts obtained via replacement of the amino hydrogen (i.e., $R^1$ and $R^2$ is hydrogen) with a compatible cation or enolation of the 3-oxo group following replacement of the amino hydrogen.

The compounds of Formula (I) exist as keto⇌enol isomers. The compounds also have an asymmetric carbon atom and can also exist as optical isomers. In some instances the compounds also exist as geometric isomers. The above formula is intended to encompass the respective individual isomers as well as mixtures thereof and the respective isomers as well as mixtures thereof are encompassed within the invention.

It has also been discovered that the presence of a 3-trifluoromethyl substituent on the 4-phenyl group of the compounds of the present invention generally very substantially enhances herbicidal activity.

In a further aspect the invention provides a herbicidal composition comprising a compatible carrier and a herbicidally effective amount of the compounds of Formula (I), or compatible salts thereof, or mixtures thereof.

The present invention also provides a method for preventing or controlling the growth of unwanted vegetation, which comprises treating the growth medium and/or the foliage of such vegetation with a herbicidally effective amount of the compound(s) of Formula (I) and/or compatible salts thereof.

In another aspect, the present invention provides a plant growth regulating composition comprising a compatible carrier and a plant growth regulating amount of the compound of Formula (I), compatible salts of Formula (I), or mixtures thereof, effective to alter the normal growth pattern of said plants.

The present invention also provides a method for regulating plant growth which comprises treating the growth medium and/or the foliage of such vegetation with a plant growth regulating effective amount of the compound(s) of Formula (I) and/or compatible salts thereof, effective to alter the normal growth pattern of said plants.

The present invention also provides chemical intermediates and processes for preparing the compounds of Formula (I).

The invention will be further described hereinbelow.

FURTHER DESCRIPTION OF THE INVENTION AND THE PREFERRED EMBODIMENTS

Illustrations of typical compounds of Formula (I) of the present invention can be had by reference to Examples 2, 3, 6–11 set forth hereinbelow on Pages 24–30 and 33–53. In terms of substituents, the preferred compounds are those wherein R is lower alkyl, aryl or substituted aryl, more preferably methyl, ethyl, propyl, phenyl or substituted phenyl, and especially phenyl, monomethylphenyl or monohalophenyl, more especially methyl, ethyl, n-propyl, 2-halophenyl, 2-lower alkylphenyl, or 4-fluorophenyl; $R^1$ and $R^2$ are independently hydrogen, methyl, ethyl or n-propyl, and more preferably one of $R^1$ or $R^2$ is hydrogen and the other is hydrogen, methyl, ethyl or n-propyl, preferably hydrogen, methyl or ethyl, especially methyl; X is hydrogen and/or Y is 3-trifluoromethyl or 3-halo, especially 3-trifluoromethyl. Most preferably the compounds contain a combination of two or more preferred substituents.

The compounds of Formula (I) wherein $R^1$ and $R^2$ are each hydrogen and R is aryl or substituted aryl and hydrohalide salts thereof can be conveniently prepared by the following schematically represented process:

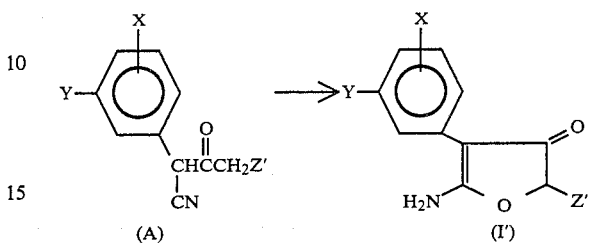

wherein X and Y are as defined hereinabove; and Z' is aryl, or substituted aryl.

Rearrangement of Compound (A) to Compound (I') can be conveniently effected by contacting Compound (A) with a halogen, preferably bromine, water and optionally a liquid carboxylic acid in the presence of an inert organic solvent.

Typically, this process is conducted at temperatures in the range of about from 0° to 100° C., preferably about from 20° to 30° C., for about from 4 to 36 hours, preferably about from 18 to 24 hours, using about from 1.0 to 10.0, preferably 1.0 to 1.1 moles of halogen per mole of Compound (A). Suitable liquid carboxylic acids which can be used include, for example, acetic acid, propionic acid, butyric acid, formic acid, and the like. By using excess carboxylic acid, the excess can serve as solvent or liquid carrier for this reaction system. Other organic solvents which can be used include, for example, liquid halogenated alkanes, for example, methylene chloride, carbon tetrachloride, chloroform, 1,2-dichloroethane; liquid aromatics, for example, benzene, toluene; liquid alkyl ethers, for example, diethylether, dimethyl, sulfoxide, dimethylformamide, and the like, and compatible mixtures thereof.

Best results are obtained using bromine as the halogen, although chlorine and iodine could also be used. Also, by using additional hydrohalide the corresponding hydrohalide addition salt of the compound of Formula (I') may be retained.

The starting materials of Formula (A) can be prepared by the following schematically represented process:

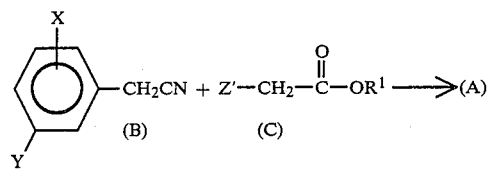

wherein $R^1$ is lower alkyl, aryl (e.g. phenyl) or arylalkylene (e.g. benzyl); and Z', Y and X are as defined hereinabove.

This process can be conveniently effected by contacting Compound (B) with Compound (C), and a strong base, preferably in an inert organic solvent.

Typically, this process is conducted at temperatures in the range of about from 0° to 100° C., preferably 75° to 85° C., for about from 5 to 36 hours, preferably 18 to 24 hours, using about from 1.0 to 10.0, preferably 1.0 to 1.2 moles of Compound (C) per mole of Compound (B). Typically, about from 1.0 to 10.0 moles of base are used per mole of Compound (C).

Suitable strong bases which can be used include, for example, alkali metal alkanolates, for example, sodium methoxide, sodium ethoxide, potassium ethoxide, sodium hydride, potassium hydride, and the like. The strong base should preferably be one which does not yield water as a by-product in this reaction system.

Suitable inert solvents which can be used include, for example, lower alkanols (for example, methanol, ethanol, and propanol) tetrahydrofuran, dimethoxyethane, dioxane, and the like, and compatible mixtures thereof. Conveniently, the alkali metal alkanolate is prepared in situ by reacting an alkali metal with excess alkanol which in turn serves as solvent for the above reaction.

The starting materials of Formulas (B) and (C) are generally known materials and can be prepared by known procedures, or obvious modifications thereof (i.e., substitution of appropriate starting materials). The preparation of Compound (B) is for example described in Org. Syn. Coll., Volume 1, 107 (1941), and the preparation of Compound (C) is described in Org. Syn. Coll., Volume 1, 270 (1941).

The compounds of Formula (I) wherein $R^1$ and $R^2$ are each hydrogen can be prepared via the general process schematically represented by the following overall reaction equation:

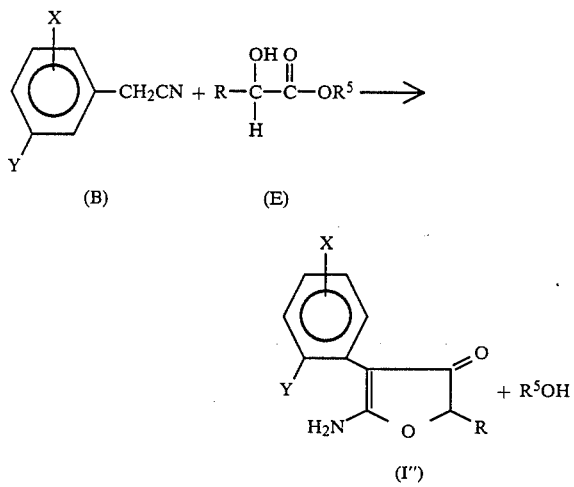

wherein R, and X and Y are as defined hereinabove; and $R^5$ is lower alkyl, aryl (e.g. phenyl) or arylalkylene (e.g. benzyl).

This process can be conveniently effected by contacting Compound (B) with Compound (E), and a strong base (e.g. sodium methoxide, sodium ethoxide), preferably in an inert organic solvent.

Typically, this process is conducted at temperatures in the range of about from 0° to 100° C., preferably 75° to 85° C. for about from 5 to 36 hours, preferably 18 to 24 hours, using about from 1.0 to 10.0, preferably 1.0 to 1.2 moles of Compound (E) per mole of Compound (B). Suitable inert organic solvents which can be used include, for example, lower alkanols (e.g. methanol, ethanol, propanol, etc.); tetrahydrofuran; dimethoxyethane; dioxane; and the like, and compatible mixtures thereof.

Suitable bases which can be used for this process include those bases previously described with respect to the reaction of Compound (B) with Compound (C).

The hydroxy esters of Formula (E) are generally known compounds and can be prepared by known procedures or by obvious modifications thereof (e.g., by using appropriately substituted starting materials).

The compounds of Formula I wherein $R^1$ and $R^2$ are hydrogen and R is alkyl, cycloalkyl, alkoxyalkyl, alkylthioalkyl, arylalkylene, substituted arylalkylene or alkenylalkyl (e.g., $-CH_2CH=CH$) can also be conveniently prepared by the following schematically represented process:

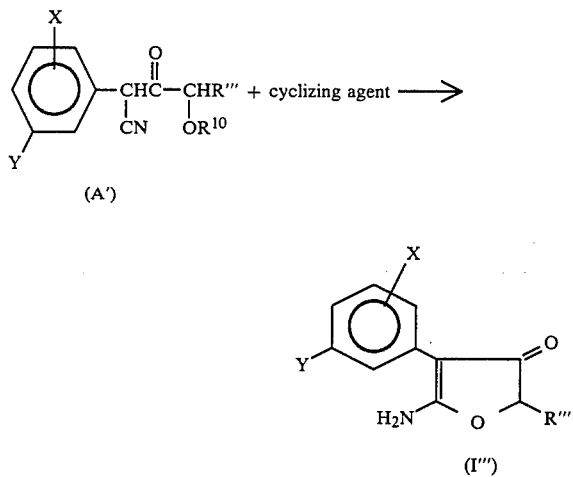

wherein R''' is alkyl, cycloalkyl, alkoxyalkyl, alkylthioalkyl, arylalkylene, substituted arylalkylene or alkenyl and $R^{10}$ is lower alkyl, preferably methyl.

This process can be conveniently effected by contacting Compound (A') with a cyclizing agent, under reactive conditions, preferably in an inert organic solvent.

Typically, this process is conducted at temperatures in the range of about from 0° to 200° C., preferably about from 115° to 120° C., for about from 10 to 120 minutes, preferably about from 10 to 30 minutes, using about from 1 to 10, preferably 1 to 2, moles of cyclizing agent per mole of Compound (A'). Suitable cyclizing agents which can be used include, for example, strong anhydrous acids, for example, sulfuric acid, hydrogen chloride, hydrogen bromide, trifluoroacetic acid, methane sulfonic acid, and the like. Best results are typically obtained using anhydrous sulfuric acid. Suitable inert organic solvents which can be used include, for example, acetic acid, propionic acid, butyric acid, toluene, xylene, and the like, and compatible mixtures thereof.

The starting materials of formula (A') can be prepared via the following schematically represented process:

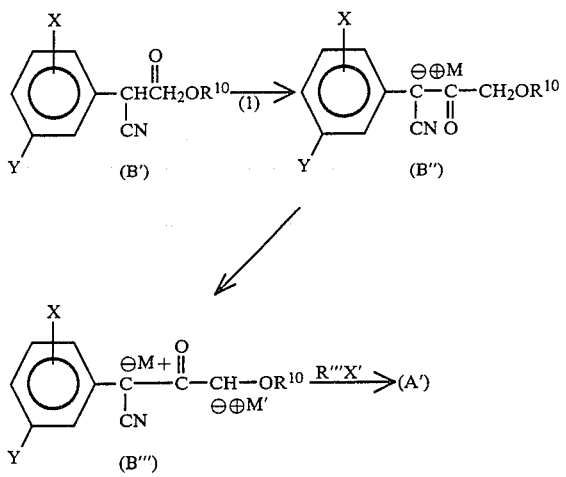

wherein R''' and $R^{10}$ are as defined hereinabove; X' is chloro, bromo or iodo and M and M' are independently sodium or lithium.

Although this process is schematically shown as three steps, the steps are typically and conveniently conducted in situ. Also as is conventional with such reactions the reactions are preferably conducted under substantially anhydrous conditions under an inert gas (e.g., nitrogen).

In the first step of this process compound (B') is contacted with a non-nucleophilic base, preferably in an inert organic solvent. This step is typically conducted at temperatures in the range of about from 0°–25° C. for about from ½ to 3 hours using about from 1 to 2, preferably 1 to 1.3, mole equivalents of non-nucleophilic base per mole of compound (B'). Suitable nonnucleophilic bases which can be used include, for example, alkali metal hydrides, e.g., sodium hydride, potassium hydride, etc.; alkali metal amides, e.g., lithium bis(trimethylsilyl)amide; sodium bis(trimethylsilyl)amide; potassium bis(trimethylsilyl)amide; lithium diethylamide, lithium diisopropyl amide; sodium dimethylamide, and the like. Sodium hydride is generally preferred as it has given very good results and is readily commercially available. The alkali metal amides, and also of course the alkali metal hydrides are generally known compounds and can be prepared by known procedures, or obvious modifications thereof. For example, the alkali metal amides can be prepared by the reaction of a secondary amine with an alkyl alkali metal.

Suitable inert organic solvents, which can be used, include, for example, tetrahydrofuran, dioxane, dimethoxyethane, diethyl ether, diisopropy ether, and the like and compatible mixtures thereof.

The second step can be effected by contacting compound (B'') with an alkyl base preferably in an inert organic solvent. As before noted, this process step is preferably conducted in situ with the reaction product mixture of the first step. Typically the second step is conducted at temperature ranges of about from −78° to 0° C. for about from 1 to 4 hours using from about 1 to 2, preferably 1 to 1.3 mole equivalents of alkyl base per mole of compound (B''). Suitable alkyl bases which can be used include for example alkyl-alkali metals, alkyl Grignard reagents, and the like. Preferably n-butyllithium is used as it gives good results and is readily commercially available. Suitable solvents which can be used include those listed above with respect to the first step and the like.

The third step can be effected by contacting compound (B''') with the appropriate R''' halide having the desired R''' group, preferably in an inert organic solvent. The third step is also typically conducted in situ with the reaction product mixture of the second step.

The third step of this process is typically conducted at temperatures in the range of about from −30° to 30° C., preferably 22° to 25° C. for about from 1 to 18 hours, preferably 1 to 5 hours using about from 1 to 10 moles, preferably 1 to 1.5 moles of R'''X' per mole of B'''. Suitable inert organic solvents include those given above with respect to the first step of this process, and the like. The R'''X' halides are generally known compounds and can be prepared by known procedures or obvious modifications thereof (e.g., substitution of appropriate reactants and solvents).

The starting materials of Formula (B') can be prepared by the following schematically represented process:

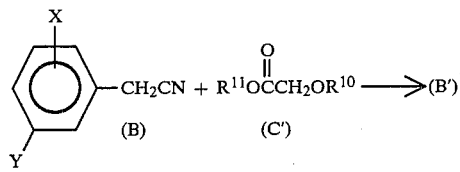

wherein $R^{11}$ is lower alkyl (preferably methyl) and $R^{10}$, Y and X are as defined hereinabove.

This process can be conveniently effected by contacting Compound (B) with Compound (C'), and a strong base under reactive conditions, preferably in an inert organic solvent.

Typically, this process is conducted using the same conditions as described hereinabove with respect to the preparation of Compound (A) save that reactant C' is used in place of reactant C. The reactants of Formula C' are simple alkyl alkoxyacetate esters, for example, methyl methoxyacetate. The preparation of such compounds is well known to the art.

The compound of Formula (I) wherein one or both of $R^1$ and $R^2$ are substituted can be prepared by alkylation of the amino group of the corresponding compounds for formula I'':

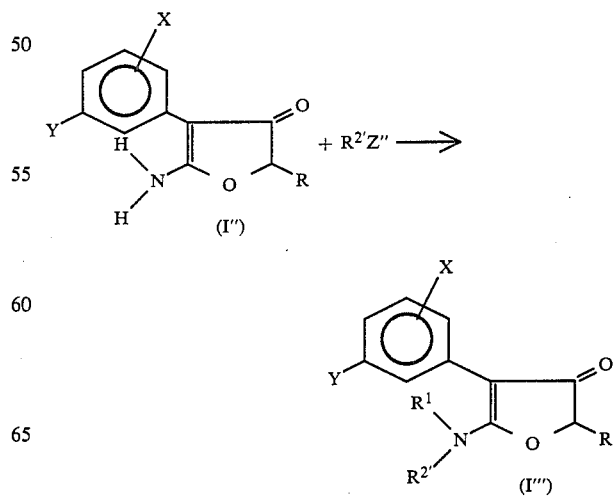

wherein R, R¹, X and Y are as defined hereinabove; and R²′ is as defined for R² but is not hydrogen; and R²′Z″ is an alkylation agent having the appropriate R²′ or appropriate R¹ group if dialkylation is desired.

This process can be effected by contacting Compound (I″) with a suitable alkylation agent capable of alkylating primary or secondary amino groups.

For example, this can be effected by contacting Compound (I″) with R²′ iodide or bromide, preferably in an inert organic solvent and preferably in the presence of a scavenger base. Typically, this process is conducted at temperatures in the range of from about 0° to 100° C., preferably 20° to 45° C. for about from 1.0 to 72.0, preferably 2.0 to 18.0 hours. Where it is desired to monoalkylate, then typically about from 1.0 to 1.1 moles of R²′ halide reactant is used per mole of Compound (I″). Where it is desired to alkylate both amino hydrogens, then typically about from 1.9 to 4.0 moles of R²′ halide are used per mole of Compound (I″). In the case where it is desired to prepare the compound wherein R²′ is alkoxyalkyl or alkylthioalkyl, it is preferred to use a large excess of R²′ halide even where monoalkylation is desired; for example 3 to 6 moles of R²′Z″ per mole of I″. Further alkylation can be effected in a second step if desired. Also variation in R¹ and R² can be effected by first alkylating only one of the two amino hydrogens and then alkylating the second amino hydrogen with an alkylating agent having a different R²′ group. The compounds wherein R¹ and R² together with the amino nitrogen atoms form a saturated heterocycle can be prepared by using the appropriate Z″—(CH₂)₂₋₅—Z″, wherein Z″ is Cl or Br alkylating agent. The R¹R²N unsaturated heterocycle can be prepared by using the appropriate cis-alkenyl dihalide, wherein one of the halo atoms is on each of the terminal alkenyl carbon. Suitable inert organic solvents which can be used, include, for example, liquid halogenated alkanes; for example, methylene chloride, carbon tetrachloride, or dichloroethane; also useful are tetrahydrofuran and the like. Suitable scavenger bases which can be used include, for example, the bases described hereinabove with respect to the reaction of Compound (B) with Compound (C).

The compounds of Formula (I‴) wherein R¹ is lower alkyl (e.g. methyl) and R² is hydrogen or lower alkyl, are advantageously prepared using dialkyl sulfate as the alkylating agent. This can be conveniently effected by contacting the compound of Formula I wherein one or both of R¹ and/or R² are hydrogen with the desired lower alkyl sulfate in the presence of a strong base and preferably in an inert organic solvent in the presence of a phase transfer agent. Typically, this process is conducted at temperatures in the range of about from 0° to 100° C., preferably 20° to 45° C., using about from 1.0 to 4.0 moles of dialkyl sulfate per mole of Compound I. An excess, typically about 2.5 mole of base is used. Preferably, this process is also conducted in an inert organic solvent such as, for example, methylene chloride, carbon tetrachloride, dichloroethane, tetrahydrofuran, and the like.

Suitable strong bases which can be used include, for example, sodium hydroxide, potassium hydroxide, sodium ethoxide, sodium carbonate, potassium carbonate, and the like. Suitable phase transfer agents are agents which transfer hydrophilic ions into a lipophilic organic medium and include, for example, benzyl triethylammonium chloride, tetra-n-butylammonium chloride, methyltrioctylammonium chloride, and the like.

The compatible salts of Formula (I) can be prepared by conventional procedures for example by treating the compound of Formula (I) wherein R¹ and/or R² are hydrogen with a suitable strong base such as, for example, n-butyllithium, sodium hydride, potassium hydride, and the like, having the desired cation, by conventional procedures to yield the corresponding R¹ and/or R² cation salts. The enolate salts can be prepared by treating the R¹ and/or R² cation salts with base via conventional procedures. The acid addition salts can be prepared by treating the free base of Formula (I) with a strong acid. Preferably the free base of Formula (I) is contacted with the strong acid as an anhydrous gas. Suitable acids include, for example, hydrogen fluoride, hydrogen chloride, hydrogen iodide, hydrogen bromide, sulfuric acid and the like. Additional variations in the salt can also be effected via ion exchange with an ion exchange resin having the desired exchange ion.

GENERAL PROCESS CONDITIONS

In the above-described processes, it is generally preferable to separate the respective products before proceeding with the next step in the reaction sequence, except where described as an in situ step or unless otherwise expressly stated. These products can be recovered from their respective reaction product mixtures by any suitable separation and purification procedure, such as, for example, recrystallization and chromatography. Suitable separation and purification procedures are, for example, illustrated in the Examples set forth hereinbelow.

Generally, the reactions described above are conducted as liquid phase reaction and hence pressure is generally not significant except as it affects temperature (boiling point) where reactions are conducted at reflux. Therefore, these reactions are generally conducted at pressures of about from 300 to 3,000 mm of mercury and conveniently are conducted at about atmospheric or ambient pressure.

It should also be appreciated that where typical or preferred process conditions (e.g., reaction temperatures, times, mole ratios of reactants, solvents, etc.) have been given, that other process conditions could also be used. Optimum reaction conditions (e.g., temperature, reaction time, mol ratios, solvents, etc.) may vary with the particular reagents or organic solvents used but can be determined by routine optimization procedures.

Where optical isomer mixtures are obtained, the respective optical isomers can be obtained by conventional resolution procedures. Geometric isomers can be separated by conventional separation procedures which depend upon differences in physical properties between the geometric isomers.

DEFINITIONS

As used herein the following terms have the following meanings unless expressly stated to the contrary:

The term "lower alkyl" refers to both straight- and branched-chain alkyl groups having a total of from 1 through 4 carbon atoms and includes primary, secondary and tertiary alkyl groups. Typical lower alkyls include, for example, methyl, ethyl, n-propyl, isopropyl, n-butyl, t-butyl.

The term "alkylene" refers to both straight chained and branched chained alkylene groups and includes, for example, —CH₂—; —CH₂—CH₂—;

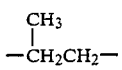

and the like.

The term "lower alkenyl" refers to alkenyl groups having 2 through 6, preferably 2 through 4, carbon atoms and includes, for example, vinyl, 1-propenyl, 2-propenyl, 1-methylvinyl, 1-butenyl, 2-methylprop-1-enyl and the like.

The term "lower alkoxy" refers to the group —OR' wherein R' is lower alkyl.

The term "lower alkylthio" refers to the group —SR' wherein R' is lower alkyl.

The term "lower alkoxyalkyl" refers to the group R'OR"— wherein R' and R" are independently straight chain or branched chain alkyl groups having 1 through 3 carbon atoms.

The term "lower alkylthioalkyl" refers to the group R'SR"— wherein R' and R" are independently straight chain or branched chain alkyl groups having 1 through 3 carbon atoms.

The term "lower alkoxycarbonylalkyl" refers to the group

wherein R' is lower alkyl and R" is alkylene having 1 through 4 carbon atoms and can be straight or branched chained. Typical alkoxycarbonylalkyl groups include for example, —CH$_2$C(O)OCH$_3$; —CH(CH$_3$)-C(O)OC$_2$H$_5$, and the like.

The term "halo" refers to the group of fluoro, chloro, bromo and iodo.

The term "lower haloalkyl" refers to haloalkyl compounds having 1 through 4 carbon atoms and 1 through 3 halo atoms independently selected from the group of fluoro, chloro, bromo and iodo. Preferably the lower haloalkyl group has 1 or 2 carbon atoms.

The term "lower haloalkoxy" refers to "lower alkoxy" groups having 1 through 3 halo atoms independently selected from the group of fluoro, chloro, bromo or iodo.

The term "aryl" refers to aryl groups having 6 through 10 carbon atoms and includes, for example, phenyl, naphthyl, indenyl. Typically the aryl group will be phenyl or naphthyl as compounds having such groups are more readily available commercially than other aryl compounds.

The term "substituted aryl" refers to aryl groups having 1 through 3 substituents independently selected from the group of lower alkyl, lower alkoxy, halonitro, or haloalkyl having 1 through 3 carbon atoms and 1 through 3 halo atoms. Typical substituted aryl groups include, for example, 2-fluorophenyl, 2-chlorophenyl, 2,6-dimethylphenyl, 4-fluorophenyl, 2-methylphenyl, 2-chloro,3-chloromethylphenyl, 2-nitro,5-methylphenyl, 2,6-dichlorophenyl, 3-trifluoromethylphenyl, 2-methoxyphenyl, 2-bromonaphth-1-yl, 3-methoxyinden-1-yl, and the like.

The term "arylalkylene" refers to the group ArR$^3$— wherein Ar is aryl and R$^3$ is alkylene having 1 through 3 carbon atoms and includes both straight-chained and branched-chained alkylenes, for example, methylene, ethyl, 1-methylethyl, and propyl.

The term "(substituted aryl)alkylene" or "ring-substituted arylalkylene" refers to the group Ar'R$^3$— wherein Ar' is substituted aryl and R$^3$ is alkylene as defined with respect to arylalkylene.

The term "saturated nitrogen heterocycle" as used herein with respect to R$^1$ and R$^2$ of formula I refers to the groups having the formula:

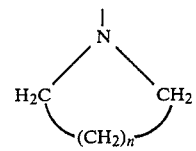

wherein n is 1, 2, or 3.

The term "unsaturated nitrogen heterocycle" as used herein with respect to R$^1$ and R$^2$ of formula I refer to the groups having the formulas:

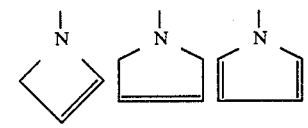

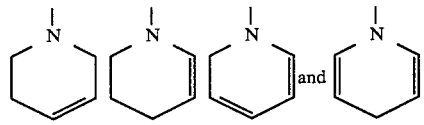

The term "compatible salts" refers to salts which do not significantly alter the herbicidal properties of the parent compound. Suitable salts include cation salts such as, for example, the cation salts of lithium, sodium, potassium, alkali earth metals, ammonia, quaternary ammonium salts; acid addition salts, for example, hydrochloride, hydrobromide, hydrofluoride, hydrosulfate salts and the like.

The term "room temperature" or "ambient temperature" refers to about 20°–25° C.

UTILITY

The compounds of Formula (I) exhibit both pre-emergence and post-emergence herbicidal activity and exhibit especially good pre-emergence herbicidal activity.

Generally, for post-emergent applications, the herbicidal compounds are applied directly to the foliage or other plant parts. For pre-emergence applications, the herbicidal compounds are applied to the growth medium, or prospective growth medium, for the plant. The optimum amount of the herbicidal compound or composition will vary with the particular plant species, and the extent of plant growth, if any, and the particular part of the plant which is contacted and the extent of contact. The optimum dosage can also vary with the general location, or environment (e.g., sheltered areas such as greenhouses compared to exposed areas such as fields), and type and degree of control desired. Generally, for both pre- and post-emergent control, the present compounds are applied at rates of about from 0.02 to 60 kg/ha, preferably about from 0.02 to 10 kg/ha.

Also, although in theory the compounds can be applied undiluted, in actual practice they are generally applied as a composition or formulation comprising an effective amount of the compound(s) and an acceptable carrier. An acceptable or compatible carrier (agriculturally acceptable carrier) is one which does not significantly adversely affect the desired biological effect achieved by the active compounds, save to dilute it. Typically, the composition contains about from 0.05 to 95% by weight of the compound of Formula (I) or mixtures thereof. Concentrates can also be made having high concentrations designed for dilution prior to application. The carrier can be a solid, liquid, or aerosol. The actual compositions can take the form of granules, powders, dusts, solutions, emulsions, slurries, aerosols, and the like.

Suitable solid carriers which can be used include, for example, natural clays (such as kaolin, attapulgite, montmorillonite, etc.), talcs, pyrophyllite, diatomaceous silica, synthetic fine silica, calcium aluminosilicate, tricalcium phosphate, and the like. Also, organic materials, such as, for example, walnut shell flour, cotton-seed hulls, wheat flour, wood flour, wood bark flour, and the like can also be used as carriers. Suitable liquid diluents which can be used include, for example, water, organic solvents (e.g., hydrocarbons such as benzene, toluene, dimethylsulfoxide, kerosene, diesel fuel, fuel oil, petroleum naphtha, etc.), and the like. Suitable aerosol carriers which can be used include conventional aerosol carriers such as halogenated alkanes, etc.

The composition can also contain various promoters and surface-active agents which enhance the rate of transport of the active compound into the plant tissue such as, for example, organic solvents, wetting agents and oils, and in the case of compositions designed for preemergence application agents which reduce the leachability of the compound or otherwise enhance soil stability.

The composition can also contain various compatible adjuvants, stabilizers, conditioners, insecticides, fungicides, and if desired, other herbicidally active compounds.

At reduced dosages the compounds of the present invention also exhibit plant growth regulating activity and can be used to alter the normal growth pattern of green plants.

The compounds of Formula (I) can be applied as plant growth regulators in pure form, but more pragmatically, as in the case of herbicidal application, are applied in combination with a carrier. The same types of carriers as set forth hereinabove with respect to the herbicidal compositions can also be used. Depending on the desired application, the plant growth regulating composition can also contain, or be applied in combination with other compatible ingredients such as desiccants, defoliants, surface-active agents, adjuvants, fungicides, and insecticides. Typically, the plant growth regulating composition will contain a total of about from 0.005 to 90 wt. % of the compound(s) of Formula (I) depending on whether the composition is intended to be applied directly or diluted first.

A further understanding of the invention can be had in the following non-limiting Preparation and Examples. Wherein, unless expressly stated to the contrary, all temperatures and temperature ranges refer to the Centigrade system and to the term "ambient" or "room temperature" refers to about 20°–25° C. The term "percent" or "%" refers to weight percent and the term "mole" or "moles" refers to gram moles. The term "equivalent" refers to a quantity of reagent equal in moles, to the moles of the preceding or succeeding reactant recited in that example in terms of finite moles or finite weight or volume. Where given, proton-magnetic resonance spectrum (p.m.r. or n.m.r.) were determined at 60 mHz, signals are assigned as singlets (s), broad singlets (bs), doublets (d), double doublets (dd), triplets (t), double triplets (dt), quartets (q), and multiplets (m); and cps refers to cycles per second. Also where necessary examples are repeated to provide additional starting material for subsequent examples.

EXAMPLES

EXAMPLE 1

(3-Trifluoromethylphenyl)-benzylcarbonyl-acetonitrile

In this example, 4.91 g of metallic sodium was added to 110 ml of anhydrous ethanol at room temperature and stirred until all of the sodium dissolved. A mixture containing 18.76 g of (3-trifluoromethylphenyl)acetonitrile and 21.73 g of ethyl phenylacetate was then added dropwise and the resulting mixture was stirred at reflux for about 18 hours. The mixture was then poured into 300 ml water and extracted three times with ethyl ether. The pH of the extracted aqueous layer was adjusted to a pH of about 1 with aqueous 10 wt. % hydrochloric acid and again extracted three times with ethyl ether. The organic layer was washed twice with saturated aqueous sodium bicarbonate, dried over magnesium sulfate and evaporated to dryness under vacuum affording 22.6 g of the title compound.

Similarly, by adapting the above procedure using the appropriately substituted-phenyl acetonitrile and ethyl-substituted phenyl acetate starting materials, the following compounds can be prepared:

(5-chloro-3-trifluoromethylphenyl)-benzylcarbonyl-acetonitrile;
(4-chloro-3-trifluoromethylphenyl)-benzylcarbonyl-acetonitrile;
(2-bromo-3-trifluoromethylphenyl)-benzylcarbonyl-acetonitrile;
(6-fluoro-3-trifluoromethylphenyl)-benzylcarbonyl-acetonitrile;
(4-methyl-3-trifluoromethylphenyl)-benzylcarbonyl-acetonitrile;
(5-methoxy-3-trifluoromethylphenyl)-benzylcarbonyl-acetonitrile;
(6-methyl-3-trifluoromethylphenyl)-benzylcarbonyl-acetonitrile;
(3,5-di-trifluoromethylphenyl)-benzylcarbonyl-acetonitrile;
(3-difluoromethoxyphenyl)-benzylcarbonyl-acetonitrile;
(3-trifluoromethoxyphenyl)-benzylcarbonyl-acetonitrile;
(3-trifluoromethylphenyl)-(4-fluorobenzylcarbonyl)-acetonitrile;
(3-trifluoromethylphenyl)-1-naphthylmethylene-acetonitrile;
(2-chloro-3-methylphenyl)-benzylcarbonyl-acetonitrile;
(4-ethyl-3-methylphenyl)-benzylcarbonyl-acetonitrile;
(5-methoxy-3-chlorophenyl)-benzylcarbonyl-acetonitrile;
(3-iodophenyl)-benzylcarbonyl-acetonitrile;
(3-difluoromethylthiophenyl)-benzylcarbonyl-acetonitrile;
(3-trifluoromethylthiophenyl)-benzylcarbonyl-acetonitrile;

(3,5-diethoxyphenyl)-benzylcarbonyl-acetonitrile;
(3-bromophenyl)-(2-nitrobenzylcarbonyl)-acetonitrile;
(2-chloro-3-methylphenyl)-benzylcarbonyl-acetonitrile;
(3-bromo-2-ethylphenyl)-naphth-1-ylmethylenecarbonyl-acetonitrile;
(2,3-dimethylphenyl)-beta-naphth-1-ylmethylcarbonyl-acetonitrile;
(3-chlorophenyl)-benzylcarbonyl-acetonitrile;
(3-methylphenyl)-benzylcarbonyl-acetonitrile;
(3-t-butoxyphenyl)-benzylcarbonyl-acetonitrile;
(3-propylphenyl)-benzylcarbonyl-acetonitrile;
(3-bromophenyl)-benzylcarbonyl-acetonitrile;
(3-iodophenyl)-(3-nitrobenzylcarbonyl)-acetonitrile;
(3-trifluoromethylphenyl)-(2,3-dichlorobenzylcarbonyl)-acetonitrile;
(3-methoxyphenyl)-1-naphthylmethylenecarbonyl-acetonitrile;
(3-trifluoromethyl)-(3-chloro-8-fluoronaphth-1-ylmethylenecarbonyl)-acetonitrile;
(3-trifluoromethyl)-[(2-trifluoromethyl-3-methyl-8-methoxy-napth-1-yl)methylenecarbonyl]-acetonitrile;
(3-trifluoromethyl)-(inden-1-ylmethylenecarbonyl)-acetonitrile; and
(3-trifluoromethyl)-(2-fluoroinden-1-yl-methylenecarbonyl)-acetonitrile.

EXAMPLE 2

2-Phenyl-3-oxo-4-(3-trifluoromethylphenyl)-5-amino-2,3-dihydrofuran

In this example a solution containing 21.8 g of (3-trifluoromethylphenyl)-benzylcarbonyl-acetonitrile, dissolved in 60 ml of acetic acid was treated dropwise with a solution of 12.65 g of bromine in 20 ml of glacial acetic acid. The reaction mixture was stirred for about 16 hours at room temperature. The reaction mixture was poured into 250 ml of water and the resulting mixture was extracted three times with ethyl ether. The organic extracts were washed with saturated aqueous sodium bicarbonate, dried over magnesium sulfate and concentrated in vacuo to yield 8.4 g of white solid which was dried affording 7.0 g of the title compound.

Similarly, by adapting the above procedure to the compounds listed in Example 1, the following compounds can be prepared:
2-phenyl-3-oxo-4-(5-chloro-3-trifluoromethylphenyl)-5-amino-2,3-dihydrofuran;
2-phenyl-3-oxo-4-(4-chloro-3-trifluoromethylphenyl)-5-amino-2,3-dihydrofuran;
2-phenyl-3-oxo-4-(2-bromo-3-trifluoromethylphenyl)-5-amino-2,3-dihydrofuran;
2-phenyl-3-oxo-4-(6-fluoro-3-trifluoromethylphenyl)-5-amino-2,3-dihydrofuran;
2-phenyl-3-oxo-4-(4-methyl-3-trifluoromethylphenyl)-5-amino-2,3-dihydrofuran;
2-phenyl-3-oxo-4-(5-methoxy-3-trifluoromethylphenyl)-5-amino-2,3-dihydrofuran;
2-phenyl-3-oxo-4-(6-methyl-3-trifluoromethylphenyl)-5-amino-2,3-dihydrofuran;
2-phenyl-3-oxo-4-(3,5-di-trifluoromethylphenyl)-5-amino-2,3-dihydrofuran;
2-phenyl-3-oxo-4-(3-difluoromethoxyphenyl)-5-amino-2,3-dihydrofuran;
2-phenyl-3-oxo-4-(3-trifluoromethoxyphenyl)-5-amino-2,3-dihydrofuran;
2-(4-fluorophenyl)-3-oxo-4-(3-trifluoromethylphenyl)-5-amino-2,3-dihydrofuran;
2-(1-naphthyl)-3-oxo-4-(3-trifluoromethylphenyl)-5-amino-2,3-dihydrofuran;
2-phenyl-3-oxo-4-(2-chloro-3-methylphenyl)-5-amino-2,3-dihydrofuran;
2-phenyl-3-oxo-4-(4-ethyl-3-methylphenyl)-5-amino-2,3-dihydrofuran;
2-phenyl-3-oxo-4-(5-methoxy-3-chlorophenyl)-5-amino-2,3-dihydrofuran;
2-phenyl-3-oxo-4-(3-iodophenyl)-5-amino-2,3-dihydrofuran;
2-phenyl-3-oxo-4-(3-difluoromethylthiophenyl)-5-amino-2,3-dihydrofuran;
2-phenyl-3-oxo-4-(3-trifluoromethylthiophenyl)-5-amino-2,3-dihydrofuran;
2-phenyl-3-oxo-4-(3,5-diethoxyphenyl)-5-amino-2,3-dihydrofuran;
2-(2-nitrophenyl)-3-oxo-4-(3-bromophenyl)-5-amino-2,3-dihydrofuran;
2-phenyl-3-oxo-4-(2-chloro-3-methylphenyl)-5-amino-2,3-dihydrofuran;
2-(1-naphthyl)-3-oxo-4-(3-bromo-2-ethylphenyl)-5-amino-2,3-dihydrofuran;
2-(1-naphthyl)-3-oxo-4-(2,3-dimethylphenyl)-5-amino-2,3-dihydrofuran;
2-phenyl-3-oxo-4-(3-chlorophenyl)-5-amino-2,3-dihydrofuran;
2-phenyl-3-oxo-4-(3-methylphenyl)-5-amino-2,3-dihydrofuran;
2-phenyl-3-oxo-4-(3-butoxyphenyl)-5-amino-2,3-dihydrofuran;
2-phenyl-3-oxo-4-(3-propylphenyl)-5-amino-2,3-dihydrofuran;
2-phenyl-3-oxo-4-(3-bromophenyl)-5-amino-2,3-dihydrofuran;
2-(3-nitrophenyl)-3-oxo-4-(3-iodophenyl)-5-amino-2,3-dihydrofuran;
2-(2,3-dichlorophenyl)-3-oxo-4-(3-trifluoromethylphenyl)-5-amino-2,3-dihydrofuran;
2-(1-naphthyl)-3-oxo-4-(3-methoxyphenyl)-5-amino-2,3-dihydrofuran;
2-(3-chloro-8-fluoronaphth-1-yl)-3-oxo-4-(3-trifluoromethylphenyl)-5-amino-2,3-dihydrofuran;
2-(2-trifluoromethyl-3-methyl-8-methoxy-naphth-1-yl)-3-oxo-4-(3-trifluoromethylphenyl)-5-amino-2,3-dihydrofuran;
2-inden-1-yl-3-oxo-4-(3-trifluoromethylphenyl)-5-amino-2,3-dihydrofuran; and
2-(2-fluoroinden-1-yl)-3-oxo-4-(3-trifluoromethylphenyl)-5-amino-2,3-dihydrofuran.

EXAMPLE 3

2-Methyl-3-oxo-4-(3-trifluoromethylphenyl)-5-amino-2,3-dihydrofuran

A dry, 500-ml, three-neck, round-bottom flask equipped with a mechanical stirrer, addition funnel and a reflux condenser was charged with 100 ml of ethanol. To the stirred solvent were added 3.5 g of sodium. After all the metal had dissolved, a solution of 13.0 g of ethyl L-(+)-lactate and 18.5 g of m-trifluoromethylphenylacetonitrile in 30 ml of ethanol was added dropwise to the reaction mixture. The mixture became a deep red and after the addition was complete, the mixture was heated at reflux overnight (about 18 hours). The mixture was then cooled to room temperature and added to 300 ml of water and the resulting mixture was acidified (pH about 1) with 10% hydrochloric acid. The mixture was then extracted with ether (three times) and the organic extracts were washed (two times) with saturated aqueous sodium bicarbonate, dried over magnesium sulfate and concentrated in vacuo to yield a thick oil. This oil was taken up in a mixture of ether/petroleum ether and the desired compound crystallized as a yellow powder. Two crops of crystals were collected to afford a total of 4.7 g of the title compound.

Similarly, by adapting the above procedure using the corresponding appropriately substituted starting materials the following compounds can be prepared:

2-ethyl-3-oxo-4-(3-trifluoromethylphenyl)-5-amino-2,3-dihydrofuran;
2-ethyl-3-oxo-4-(5-chloro-3-trifluoromethylphenyl)-5-amino-2,3-dihydrofuran;
2-cyclopentyl-3-oxo-4-(3-trifluoromethylphenyl)-5-amino-2,3-dihydrofuran;
2-vinyl-3-oxo-4-(3-trifluoromethylphenyl)-5-amino-2,3-dihydrofuran;
2-allyl-3-oxo-4-(3-trifluoromethylphenyl)-5-amino-2,3-dihydrofuran;
2-allyl-3-oxo-4-(2-methoxy-3-trifluoromethylphenyl)-5-amino-2,3-dihydrofuran;
2-trifluoromethyl-3-oxo-4-(3-trifluoromethylphenyl)-5-amino-2,3-dihydrofuran;
2-methyl-3-oxo-4-(3-difluoromethoxyphenyl)-5-amino-2,3-dihydrofuran;
2-methyl-3-oxo-4-(3-trifluoromethoxyphenyl)-5-amino-2,3-dihydrofuran;
2-(2-chlorovinyl)-3-oxo-4-(3-trifluoromethylphenyl)-5-amino-2,3-dihydrofuran;
2-(2-chlorovinyl)-3-oxo-4-(5-propoxy-3-trifluoromethylphenyl)-5-amino-2,3-dihydrofuran;
2-methyl-3-oxo-4-(2-methoxy-3-chlorophenyl)-5-amino-2,3-dihydrofuran;
2-ethyl-3-oxo-4-(2-chloro-3-fluorophenyl)-5-amino-2,3-dihydrofuran;
2-vinyl-3-oxo-4-(3-methyl-4-methoxyphenyl)-5-amino-2,3-dihydrofuran;
2-allyl-3-oxo-4-(3,6-dimethylphenyl)-5-amino-2,3-dihydrofuran;
2-trifluoromethyl-3-oxo-4-(3-trifluoromethyl-4-bromophenyl)-5-amino-2,3-dihydrofuran;
2-(2-chlorovinyl)-3-oxo-4-(3-nitro-4-methylphenyl)-5-amino-2,3-dihydrofuran;
2-methyl-3-oxo-4-(3-methoxyphenyl)-5-amino-2,3-dihydrofuran;
2-methyl-3-oxo-4-(3-difluoromethylthiophenyl)-5-amino-2,3-dihydrofuran;
2-methyl-3-oxo-4-(3-trifluoromethylthiophenyl)-5-amino-2,3-dihydrofuran;
2-ethyl-3-oxo-4-(3-chlorophenyl)-5-amino-2,3-dihydrofuran;
2-vinyl-3-oxo-4-(3-methylphenyl)-5-amino-2,3-dihydrofuran;
2-allyl-3-oxo-4-[3,5-di(trifluoromethyl)-phenyl]-5-amino-2,3-dihydrofuran;
2-trifluoromethyl-3-oxo-4-(4-fluorophenyl)-5-amino-2,3-dihydrofuran;
2-(2-chlorovinyl)-3-oxo-4-(2-bromophenyl)-3-oxo-5-amino-2,3-dihydrofuran;
2-propyl-3-oxo-4-(2-methoxy-3-chlorophenyl)-5-amino-2,3-dihydrofuran;
2-butyl-3-oxo-4-(2-chloro-3-fluorophenyl)-5-amino-2,3-dihydrofuran;
2-vinyl-3-oxo-4-(3-chloro-4-methoxyphenyl)-5-amino-2,3-dihydrofuran;
2-allyl-3-oxo-4-(3,5-dimethylphenyl)-5-amino-2,3-dihydrofuran;
2-(trifluoromethyl)-3-oxo-4-(3-trifluoromethyl-5-bromophenyl)-5-amino-2,3-dihydrofuran;
2-(2-chlorovinyl)-3-oxo-4-(3-fluoro-4-methylphenyl)-3-oxo-5-amino-2,3-dihydrofuran;
2-phenyl-3-oxo-4-(3-methoxyphenyl)-5-amino-2,3-dihydrofuran;
2-methyl-3-oxo-4-(3,5-difluorophenyl)-5-amino-2,3-dihydrofuran;
2-vinyl-3-oxo-4-(3,5-diethylphenyl)-5-amino-2,3-dihydrofuran;
2-allyl-3-oxo-4-(3-propoxyphenyl)-5-amino-2,3-dihydrofuran;
2-trifluoromethyl-3-oxo-4-(3-fluorophenyl)-5-amino-2,3-dihydrofuran;
2-propyl-3-oxo-4-(3-bromophenyl)-3-oxo-5-amino-2,3-dihydrofuran;
2-phenyl-3-oxo-4-(2-iodo-3-fluorophenyl)-5-amino-2,3-dihydrofuran;
2-benzyl-3-oxo-4-(2-isopropoxy-3-trifluoromethylphenyl)-5-amino-2,3-dihydrofuran;
2-(3-chlorophenyl)-3-oxo-4-(2,3-dimethylphenyl)-5-amino-2,3-dihydrofuran;
2-naphth-1-yl-3-oxo-4-(3-trifluoromethyl-4-bromophenyl)-5-amino-2,3-dihydrofuran;
2-(3-methylphenyl)-3-oxo-4-(3-butyl-4-methylphenyl)-3-oxo-5-amino-2,3-dihydrofuran;
2-(3-fluorophenyl)-3-oxo-4-(3-chlorophenyl)-5-amino-2,3-dihydrofuran;
2-(2,3,5-trifluorophenyl-3-oxo-4-(3-trifluoromethylphenyl)-5-amino-2,3-dihydrofuran;
2-(3-methylnaphth-1-yl)-3-oxo-4-(3-trifluoromethylphenyl)-5-amino-2,3-dihydrofuran;
2-(2'-chlorovinyl-3-oxo-4-(3-trifluoromethylphenyl)-5-amino-2,3-dihydrofuran;
2-fluoromethyl-3-oxo-4-(3-trifluoromethylphenyl)-5-amino-2,3-dihydrofuran;
2-methoxymethylene-3-oxo-4-(3-trifluoromethylphenyl)-5-amino-2,3-dihydrofuran;
2-propoxymethylene-3-oxo-4-(3-trifluoromethylphenyl)-5-amino-2,3-dihydrofuran;
2-ethoxymethylene-3-oxo-4-(3-trifluoromethylphenyl)-5-amino-2,3-dihydrofuran;
2-(2-methoxypropyl)-3-oxo-4-(3-trifluoromethylphenyl)-5-amino-2,3-dihydrofuran;
2-methylthiomethylene-3-oxo-4-(3-trifluoromethylphenyl)-5-amino-2,3-dihydrofuran; and
2-(1-propylthioethyl)-3-oxo-4-(3-trifluoromethylphenyl)-5-amino-2,3-dihydrofuran.

EXAMPLE 4

(3-Trifluoromethylphenyl)-methoxyacetyl-acetonitrile

In this example 5.6 grams of metallic sodium was added to 120 ml of anhydrous ethanol at room temperature under a nitrogen atmosphere resulting in the evolution of hydrogen. After evolution of hydrogen was completed a mixture containing 30 g of (3-trifluoromethylphenyl)-acetonitrile and 18.5 g of methyl methoxyacetate in anhydrous ethanol was added and the resulting mixture refluxed for 3 to 4 hours. The mixture was then added to 300 ml of water and extracted three times with petroleum ether. The remaining aqueous phase was acidified with aqueous 10% hydrochloric acid to about pH 1 and extracted three times with ethyl ether. The ethyl ether extracts were combined, washed twice with saturated aqueous sodium bicarbonate, dried over magnesium sulfate and concentrated by evaporation. The concentrate was evaporated under high vacuum affording an oil which was triturated with ethyl ether. This mixture was then filtered to remove solids and the filtrate evaporated under vacuum affording 36.9 g of the title compound as a brown solid.

Similarly, by adapting the above procedure but using other (substituted and disubstituted phenyl) acetonitriles in place of (3-trifluoromethylphenyl)acetonitrile the corresponding substituted and disubstituted phenyl analogs of the title compound can be prepared.

EXAMPLE 5

(3-Trifluoromethyphenyl)-2-methoxyisovaleryl-acetonitrile

In this example 10 g of (3-trifluoromethylphenyl)-methoxyacetyl-acetonitrile was added dropwise to a slurry of 1.87 g of sodium hydride in 20 ml of tetrahydrofuran at about 0° C. under a nitrogen atmosphere, resulting in the evolution of hydrogen. After no further evolution of hydrogen was observed, the mixture was cooled to about −78° C. and 24.3 ml of 1.6M n-butyllithium in hexane was added dropwise. The mixture was stirred for 1½ hours at −78° C. and then stirred at about 0°-4° C. for twenty minutes. After this 3.9 ml (about 6.64 g) of 2-iodopropane was added dropwise and the mixture stirred overnight (about 14-16 hours). The mixture was then added to water, acidified with aqueous 10% hydrochloric acid and extracted three times with ethyl ether. The extracts were combined, dried over magnesium sulfate and concentrated under vacuum affording 11.4 g of the title compound as an oil.

Similarly, by adapting the same procedure but using the appropriate alkyl, aryl or substituted aryl, iodide, bromide, or chloride in place of iodopropane the following compounds can be prepared:

(3-trifluoromethylphenyl)-(2-methoxy-3-phenylpropionyl)acetonitrile;
(3-trifluoromethylphenyl)-[2-methoxy-3-(2-fluorophenyl)propionyl]acetonitrile;
(3-trifluoromethylphenyl)-[2-methoxy-3-(3-methylphenyl)propionyl]acetonitrile;
(3-trifluoromethylphenyl)-[2-methoxy-3-(2-ethoxyphenyl)propionyl]acetonitrile;
(3-trifluoromethylphenyl)-[2-methoxy-3-(3-nitrophenyl)propionyl]acetonitrile;
(3-trifluoromethylphenyl)-[2-methoxy-3-(2-trifluoromethylphenyl)propionyl]acetonitrile;
(3-trifluoromethylphenyl)-[2-methoxy-3-(2-chloro-3-propylphenyl)propionyl]acetonitrile;
(3-trifluoromethylphenyl)-[2-methoxy-3-(2-nitro-3-methoxyphenyl)propionyl]acetonitrile;
(3-trifluoromethylphenyl)-[2-methoxy-3-(2-fluoro-3-2′,2′-dichloroethylphenyl)propionyl]acetonitrile;
(3-trifluoromethylphenyl)-[2-methoxy-3-(2,3-dichloro-6-methylphenyl)propionyl]acetonitrile;
(3-trifluoromethylphenyl)-(2-methoxy-4-phenylbutyryl)acetonitrile;
(3-trifluoromethylphenyl)-[2-methoxy-5-(2-bromophenyl)valeryl]acetonitrile;
(3-trifluoromethylphenyl)-(2-methoxy-3-methyl-4-phenylbutyryl)acetonitrile;
(3-trifluoromethyl)-(2-methoxy-3-naphth-1-ylpropionyl)acetonitrile;
(3-trifluoromethyl)-[2-methoxy-3-(2-fluoronaphth-1-yl)propionyl]acetonitrile;
(3-trifluoromethyl)-[2-methoxy-3-(3-butylnaphth-1-yl)propionyl]acetonitrile;
(3-trifluoromethyl)-[2-methoxy-3-(5-methoxynaphth-1-yl)propionyl]acetonitrile;
(3-trifluoromethyl)-[2-methoxy-3-(6-nitronaphth-1-yl)propionyl]acetonitrile;
(3-trifluoromethyl)-[2-methoxy-3-(7-trifluoromethylnaphth-1-yl)propionyl]acetonitrile;
(3-trifluoromethyl)-[2-methoxy-3-(2-chloro-8-methylnaphth-1-yl)propionyl]acetonitrile;
(3-trifluoromethyl)-[2-methoxy-3-(3-methoxy-5-nitro-7-fluoromethylnaphth-1-yl)propionyl]acetonitrile;
(3-trifluoromethyl)-(2-methoxy-4-naphth-1-ylbutyryl)acetonitrile;
(3-trifluoromethyl)-[2-methoxy-5-(8-fluoronaphth-1-yl)valeryl]acetonitrile;
(3-trifluoromethyl)-[2-methoxy-3-methyl-3-(7-methoxynaphth-1-yl)propionyl]acetonitrile;
(3-trifluoromethylphenyl)-(2-methoxy-3-inden-1-ylpropionyl)acetonitrile; and
(3-trifluoromethylphenyl)-[2-methoxy-3-(2-fluoroinden-1-yl)propionyl]acetonitrile.

Similarly, by adapting the above procedure using other (mono or disubstited phenyl)-(methoxyacetyl)acetonitriles in place of (3-trifluoromethylphenyl)-(2-methoxyacetyl)acetonitrile the corresponding mono or disubstituted phenyl derivatives of the above compounds can be prepared.

EXAMPLE 6

2-Isopropyl-3-oxo-4-(3-trifluoromethylphenyl)-5-amino-2,3-dihydrofuran

In this example, a mixture containing 11.4 g of (3-trifluoromethylphenyl)-(2-methoxyisovaleryl)acetonitrile and 7.8 g of concentrated sulfuric acid in 50 ml of acetic acid was warmed to reflux for 30 minutes and then concentrated by evaporation under vacuum. The concentrate was mixed with diethylether, washed three times with 1N aqueous sodium hydroxide, dried over magnesium sulfate and concentrated by evaporation affording an oil. The oil was triturated in 20% (vol.) ethyl acetate:80% petroleum ether and allowed to stand overnight (14-16 hours). The solids were collected by filtration and washed three times with 20% (vol.) ethyl acetate:80% petroleum ethyl affording 2.9 g of the title compound.

Similarly, by adapting the above procedure using the other compound, products indicated in Example 5 the following compounds can be prepared:
2-benzyl-3-oxo-4-(3-trifluoromethylphenyl)-5-amino-2,3-dihydrofuran;
2-(2-fluorobenzyl)-3-oxo-4-(3-trifluoromethylphenyl)-5-amino-2,3-dihydrofuran;
2-(3-methylbenzyl)-3-oxo-4-(3-trifluoromethylphenyl)-5-amino-2,3-dihydrofuran;
2-(2-ethoxybenzyl)-3-oxo-4-(3-trifluoromethylphenyl)-5-amino-2,3-dihydrofuran;
2-(3-nitrobenzyl)-3-oxo-4-(3-trifluoromethylphenyl)-5-amino-2,3-dihydrofuran;
2-(4-fluorobenzyl)-3-oxo-4-(3-trifluoromethylphenyl)-5-amino-2,3-dihydrofuran;
2-(2-trifluoromethylbenzyl)-3-oxo-4-(3-trifluoromethylphenyl)-5-amino-2,3-dihydrofuran;
2-(2-chloro-3-propylphenyl)-3-oxo-4-(3-trifluoromethylphenyl)-5-amino-2,3-dihydrofuran;
2-(2-nitro-3-methoxyphenyl)-3-oxo-4-(3-trifluoromethylphenyl)-5-amino-2,3-dihydrofuran;
2-(2-fluoro-3-2′,2′-dichloroethylbenzyl)-3-oxo-4-(3-trifluoromethylphenyl)-5-amino-2,3-dihydrofuran;

2-(2,3-dichloro-6-methylbenzyl)-3-oxo-4-(3-tri-
fluoromethylphenyl)-5-amino-2,3-dihydrofuran;
2-(beta-phenethyl)-3-oxo-4-(3-trifluoromethylphenyl)-
5-amino-2,3-dihydrofuran;
2-[3-(2-bromophenyl)propyl]-3-oxo-4-(3-trifluorome-
thylphenyl)-5-amino-2,3-dihydrofuran;
2-[1-methyl-2-(phenyl)ethyl]-3-oxo-4-(3-trifluorome-
thylphenyl)-5-amino-2,3-dihydrofuran;
2-naphth-1-ylmethylene-3-oxo-4-(3-trifluoromethyl-
phenyl)-5-amino-2,3-dihydrofuran;
2-(2-fluoronaphth-1-ylmethylene)-3-oxo-4-(3-tri-
fluoromethylphenyl)-5-amino-2,3-dihydrofuran;
2-(3-butylnaphth-1-ylmethylene)-3-oxo-4-(3-tri-
fluoromethylphenyl)-5-amino-2,3-dihydrofuran;
2-(5-methoxynaphth-1-ylmethylene)-3-oxo-4-(3-tri-
fluoromethylphenyl)-5-amino-2,3-dihydrofuran;
2-(6-nitronaphth-1-ylmethylene)-3-oxo-4-(3-tri-
fluoromethylphenyl)-5-amino-2,3-dihydrofuran;
2-(7-trifluoromethylnaphth-1-ylmethylene)-3-oxo-4-(3-
trifluoromethylphenyl)-5-amino-2,3-dihydrofuran;
2-(2-chloro-8-methylnaphth-1-ylmethylene)-3-oxo-4-(3-
trifluoromethylphenyl)-5-amino-2,3-dihydrofuran;
2-(3-methoxy-5-nitro-7-fluoromethylnaphth-1-yl)-3-
oxo-4-(3-trifluoromethylphenyl)-5-amino-2,3-dihy-
drofuran;
2-(beta-naphth-1-ylethyl)-3-oxo-4-(3-trifluoromethyl-
phenyl)-5-amino-2,3-dihydrofuran;
2-[beta-(8-fluoronaphth-1-yl)ethyl]-3-oxo-4-(3-tri-
fluoromethylphenyl)-5-amino-2,3-dihydrofuran;
2-[1-(7-methoxynaphth-1-yl)ethyl]-3-oxo-4-(3-tri-
fluoromethylphenyl)-5-amino-2,3-dihydrofuran;
2-inden-1-ylmethylene-3-oxo-4-(3-trifluoromethyl-
phenyl)-5-amino-2,3-dihyrofuran; and
2-(2-fluoroinden-1-ylmethylene)-3-oxo-4-(3-tri-
fluoromethylphenyl)-5-amino-2,3-dihyrofuran.

Similarly, by adapting the above procedure using the corresponding mono- and disubstituted analogs of the starting materials for the above compounds the corresponding 4-(3-methylphenyl); 4-(3-beta-fluoroethox-yphenyl); 4-(3-difluoromethylenethiophenyl); 4-(3-chlorophenyl); 4-(2-bromo-3-trifluoromethylphenyl)- and 4-(2-methyl-3-difluoromethylenethiophenyl ana-logs of the above compounds can be prepared.

EXAMPLE 7

2-Phenyl-3-oxo-4-(-3-trifluoromethylphenyl)-5-
methylamino-2,3-dihydrofuran

In this example about 1 g of solid sodium hydroxide in 4.0 ml of water was added to a mixture of 3 g of 2-phenyl-3-oxo-4-(3-trifluoromethylphenyl)-5-amino-2,3-dihydrofuran in 50 ml of methylene chloride at room temperature followed by the addition of 1.19 g of dimethyl sulfate and 0.21 g of benzyltriethyl ammonium chloride. The resulting two-phase mixture was stirred at room temperature for about two hours and then washed three times with water, dried over magnesium sulfate and then concentrated by evaporation under vacuum. The residue was then purified by chromatography over silica gel eluting with mixtures of tetrahydrofuran and chloroform affording the title compound.

Similarly, by adapting the above procedure using the products listed in Examples 2, 3 and 6 as starting materials, the corresponding 5-methylamino homologs thereof can be prepared, for example:
2-phenyl-3-oxo-4-(5-chloro-3-trifluoromethylphenyl)-5-
methylamino-2,3-dihydrofuran;
2-phenyl-3-oxo-4-(4-chloro-3-trifluoromethylphenyl)-5-
methylamino-2,3-dihydrofuran;
2-phenyl-3-oxo-4-(2-bromo-3-trifluoromethylphenyl)-5-
methylamino-2,3-dihydrofuran;
2-phenyl-3-oxo-4-(6-fluoro-3-trifluoromethylphenyl)-5-
methylamino-2,3-dihydrofuran;
2-phenyl-3-oxo-4-(4-methyl-3-trifluoromethylphenyl)-
5-methylamino-2,3-dihydrofuran;
2-phenyl-3-oxo-4-(5-methoxy-3-trifluoromethyl-
phenyl)-5-methylamino-2,3-dihydrofuran;
2-phenyl-3-oxo-4-(6-methyl-3-trifluoromethylphenyl)-
5-methylamino-2,3-dihydrofuran;
2-phenyl-3-oxo-4-(3,5-di-trifluoromethylphenyl)-5-
methylamino-2,3-dihydrofuran;
2-phenyl-3-oxo-4-(3-difluoromethoxyphenyl)-5-
methylamino-2,3-dihydrofuran;
2-phenyl-3-oxo-4-(3-trifluoromethoxyphenyl)-5-
methylamino-2,3-dihydrofuran;
2-phenyl-3-oxo-4-(3-trifluoromethylthiophenyl)-5-
methylamino-2,3-dihydrofuran;
2-(4-fluorophenyl)-3-oxo-4-(3-trifluoromethylphenyl)-
5-methylamino-2,3-dihydrofuran;
2-(1-naphthyl)-3-oxo-4-(3-trifluoromethylphenyl)-5-
methylamino-2,3-dihydrofuran;
2-phenyl-3-oxo-4-(2-chloro-3-methylphenyl)-5-
methylamino-2,3-dihydrofuran;
2-phenyl-3-oxo-4-(4-ethyl-3-methylphenyl)-5-
methylamino-2,3-dihydrofuran;
2-phenyl-3-oxo-4-(5-methoxy-3-chlorophenyl)-5-
methylamino-2,3-dihydrofuran;
2-phenyl-3-oxo-4-(3-iodophenyl)-5-methylamino-2,3-
dihydrofuran;
2-phenyl-3-oxo-4-(3-difluoromethylthiophenyl)-5-
methylamino-2,3-dihydrofuran;
2-phenyl-3-oxo-4-(3-trifluoromethylthiophenyl)-5-
methylamino-2,3-dihydrofuran;
2-phenyl-3-oxo-4-(3,5-diethoxyphenyl)-5-methylamino-
2,3-dihydrofuran;
2-(2-nitrophenyl)-3-oxo-4-(3-bromophenyl)-5-
methylamino-2,3-dihydrofuran;
2-phenyl-3-oxo-4-(2-chloro-3-methylphenyl)-5-
methylamino-2,3-dihydrofuran;
2-(1-naphthyl)-3-oxo-4-(3-bromo-2-ethylphenyl)-5-
methylamino-2,3-dihydrofuran;
2-(1-naphthyl)-3-oxo-4-(2,3-dimethylphenyl)-5-
methylamino-2,3-dihydrofuran;
2-phenyl-3-oxo-4-(3-chlorophenyl)-5-methylamino-2,3-
dihydrofuran;
2-phenyl-3-oxo-4-(3-methylphenyl)-5-methylamino-2,3-
dihydrofuran;
2-phenyl-3-oxo-4-(3-butoxyphenyl)-5-methylamino-2,3-
dihydrofuran;
2-phenyl-3-oxo-4-(2-propylphenyl)-5-methylamino-2,3-
dihydrofuran;
2-phenyl-3-oxo-4-(3-bromophenyl)-5-methylamino-2,3-
dihydrofuran;
2-(3-nitrophenyl)-3-oxo-4-(3-iodophenyl)-5-
methylamino-2,3-dihydrofuran;
2-(2,3-dichlorobenzyl)-3-oxo-4-(2-trifluoromethyl-
phenyl)-5-methylamino-2,3-dihydrofuran;
2-(1-naphthyl)-3-oxo-4-(3-methoxyphenyl)-5-
methylamino-2,3-dihydrofuran;
2-(3-chloro-8-fluoronaphth-1-yl)-3-oxo-4-(3-tri-
fluoromethylphenyl)-5-methylamino-2,3-dihydrofu-
ran;
2-(2-trifluoromethyl-3-methyl-8-methoxynaphth-1-yl)-
3-oxo-4-(3-trifluoromethylphenyl)-5-methylamino-
2,3-dihydrofuran;

2-inden-1-yl-3-oxo-4-(3-trifluoromethylphenyl)-5-methylamino-2,3-dihydrofuran;
2-(2-fluoroinden-1-yl)-3-oxo-4-(3-trifluoromethylphenyl)-5-methylamino-2,3-dihydrofuran;
2-methyl-3-oxo-4-(3-trifluoromethylphenyl)-5-methylamino-2,3-dihydrofuran;
2-ethyl-3-oxo-4-(3-trifluoromethylphenyl)-5-methylamino-2,3-dihydrofuran;
2-ethyl-3-oxo-4-(5-chloro-3-trifluoromethylphenyl)-5-methylamino-2,3-dihydrofuran;
2-cyclopentyl-3-oxo-4-(3-trifluoromethylphenyl)-5-methylamino-2,3-dihyrofuran;
2-vinyl-3-oxo-4-(3-trifluoromethylphenyl)-5-methylamino-2,3-dihydrofuran;
2-allyl-3-oxo-4-(3-trifluoromethylphenyl)-5-methylamino-2,3-dihydrofuran;
2-allyl-3-oxo-4-(2-methoxy-3-trifluoromethylphenyl)-5-methylamino-2,3-dihydrofuran;
2-trifluoromethyl-3-oxo-4-(3-trifluoromethylphenyl)-5-methylamino-2,3-dihydrofuran;
2-methyl-3-oxo-4-(3-difluoromethoxyphenyl)-5-methylamino-2,3-dihydrofuran;
2-methyl-3-oxo-4-(3-trifluoromethoxyphenyl)-5-methylamino-2,3-dihydrofuran;
2-(2-chlorovinyl)-3-oxo-4-(3-trifluoromethylphenyl)-5-methylamino-2,3-dihydrofuran;
2-(2-chlorovinyl)-3-oxo-4-(5-nitro-3-trifluoromethylphenyl)-5-methylamino-2,3-dihydrofuran;
2-methyl-3-oxo-4-(2-methoxy-3-chlorophenyl)-5-methylamino-2,3-dihydrofuran;
2-ethyl-3-oxo-4-(2-chloro-3-fluorophenyl)-5-methylamino-2,3-dihydrofuran;
2-vinyl-3-oxo-4-(3-methyl-4-methoxyphenyl)-5-methylamino-2,3-dihydrofuran;
2-allyl-3-oxo-4-(3,6-dimethylphenyl)-5-methylamino-2,3-dihydrofuran;
2-trifluoromethyl-3-oxo-4-(3-trifluoromethyl-4-bromophenyl)-5-methylamino-2,3-dihydrofuran;
2-(2-chlorovinyl)-3-oxo-4-(3-nitro-4-methylphenyl)-3-oxo-5-methylamino-2,3-dihydrofuran;
2-methyl-3-oxo-4-(3-methoxyphenyl)-5-methylamino-2,3-dihydrofuran;
2-methyl-3-oxo-4-(3-difluoromethylthiophenyl)-5-methylamino-2,3-dihydrofuran;
2-methyl-3-oxo-4-(3-trifluoromethylthiophenyl)-5-methylamino-2,3, dihydrofuran;
2-ethyl-3-oxo-4-(3-chlorophenyl)-5-methylamino-2,3-dihydrofuran;
2-vinyl-3-oxo-4-(3-methylphenyl)-5-methylamino-2,3-dihydrofuran;
2-allyl-3-oxo-4-[3,5-di(trifluoromethyl)phenyl]-5-methylamino-2,3-dihydrofuran;
2-trifluoromethyl-3-oxo-4-(4-fluorophenyl)-5-methylamino-2,3-dihydrofuran;
2-(2-chlorovinyl)-3-oxo-4-(2-bromophenyl)-3-oxo-5-methylamino-2,3-dihydrofuran;
2-propyl-3-oxo-4-(2-methoxy-3-chlorophenyl)-5-methylamino-2,3-dihydrofuran;
2-butyl-3-oxo-4-(2-chloro-3-fluorophenyl)-5-methylamino-2,3-dihydrofuran;
2-vinyl-3-oxo-4-(3-chloro-4-methoxyphenyl)-5-methylamino-2,3-dihydrofuran;
2-allyl-3-oxo-4-(3,6-dimethylphenyl)-5-methylamino-2,3-dihydrofuran;
2-trifluoromethyl-3-oxo-4-(3-trifluoromethyl-5-bromophenyl)-5-methylamino-2,3-dihydrofuran;
2-(2-chlorovinyl)-3-oxo-4-(3-fluoro-4-methylphenyl)-3-oxo-5-methylamino-2,3-dihydrofuran;
2-phenyl-3-oxo-4-(3-methoxyphenyl)-5-methylamino-2,3-dihydrofuran;
2-methyl-3-oxo-4-(3,5-difluorophenyl)-5-methylamino-2,3-dihydrofuran;
2-vinyl-3-oxo-4-(3,5-diethylphenyl)-5-methylamino-2,3-dihydrofuran;
2-allyl-3-oxo-4-(3-propoxyphenyl)-5-methylamino-2,3-dihydrofuran;
2-trifluoromethyl-3-oxo-4-(3-fluorophenyl)-5-methylamino-2,3-dihydrofuran;
2-propyl-3-oxo-4-(2-bromophenyl)-3-oxo-5-methylamino-2,3-dihydrofuran;
2-phenyl-3-oxo-4-(2-iodo-3-fluorophenyl)-5-methylamino-2,3-dihydrofuran;
2-benzyl-3-oxo-4-(2-isopropoxy-3-trifluoromethylphenyl)-5-methylamino-2,3-dihydrofuran;
2-(3-chlorophenyl)-3-oxo-4-(2,3-dimethylphenyl)-5-methylamino-2,3-dihydrofuran;
2-naphth-1-yl-3-oxo-4-(3-trifluoromethyl-4-bromophenyl)-5-methylamino-2,3-dihydrofuran;
2-(3-methylphenyl)-3-oxo-4-(3-butyl-4-methylphenyl)-3-oxo-5-methylamino-2,3-dihydrofuran;
2-(3-fluorophenyl)-3-oxo-4-(3-chlorophenyl)-5-methylamino-2,3-dihydrofuran;
2-(2,3,5-trifluorophenyl)-3-oxo-4-(3-trifluoromethylphenyl)-5-methylamino-2,3-dihydrofuran; and
2-(3-methylnaphth-1-yl)-3-oxo-4-(3-trifluoromethylphenyl)-5-methylamino-2,3-dihydrofuran;
2-(1'-chlorovinyl)-3-oxo-4-(3-trifluoromethylphenyl)-5-methylamino-2,3-dihydrofuran;
2-fluoromethyl-3-oxo-4-(3-trifluoromethylphenyl)-5-methylamino-2,3-dihydrofuran;
2-methoxymethylene-3-oxo-4-(3-trifluoromethylphenyl)-5-methylamino-2,3-dihydrofuran;
2-propoxymethylene-3-oxo-4-(3-trifluoromethylphenyl)-5-methylamino-2,3-dihydrofuran;
2-ethoxymethylene-3-oxo-4-(3-trifluoromethylphenyl)-5-methylamino-2,3-dihydrofuran;
2-(2-methoxypropyl)-3-oxo-4-(3-trifluoromethylphenyl)-5-methylamino-2,3-dihydrofuran;
2-methylthiomethylene-3-oxo-4-(3-trifluoromethylphenyl)-5-methylamino-2,3-dihydrofuran; and
2-(1-propylthioethyl)-3-oxo-4-(3-trifluoromethylphenyl)-5-methylamino-2,3-dihydrofuran.
2-benzyl-3-oxo-4-(3-trifluoromethylphenyl)-5-methylamino-2,3-dihydrofuran;
2-(2-fluorobenzyl)-3-oxo-4-(3-trifluoromethylphenyl)-5-methylamino-2,3-dihydrofuran;
2-(3-methylbenzyl)-3-oxo-4-(3-trifluoromethylphenyl)-5-methylamino-2,3-dihydrofuran;
2-(2-ethoxybenzyl)-3-oxo-4-(3-trifluoromethylphenyl)-5-methylamino-2,3-dihydrofuran;
2-(3-nitrobenzyl)-3-oxo-4-(3-trifluoromethylphenyl)-5-methylamino-2,3-dihydrofuran;
2-(4-fluorobenzyl)-3-oxo-4-(3-trifluoromethylphenyl)-5-methylamino-2,3-dihydrofuran;
2-(2-trifluoromethylbenzyl)-3-oxo-4-(3-trifluoromethylphenyl)-5-methylamino-2,3-dihydrofuran;
2-(chloro-3-propylphenyl)-3-oxo-4-(3-trifluoromethylpheny)-5-methylamino-2,3-dihydrofuran;
2-(2-nitro-3-methoxyphenyl)-3-oxo-4-(3-trifluoromethylphenyl)-5-methylamino-2,3-dihydrofuran;
2-(2-fluoro-3-2',2'-dichloroethylbenzyl)-3-oxo-4-(3-trifluoromethylphenyl)-5-methylamino-2,3-dihydrofuran;
2-(2,3-dichloro-6-methylbenzyl)-3-oxo-4-(3-trifluoromethylphenyl)-5-methylamino-2,3-dihydrofuran;

2-(beta-phenethyl)-3-oxo-4-(3-trifluoromethylphenyl)-5-methylamino-2,3-dihydrofuran;

2-[3-(2-bromophenyl)propyl]-3-oxo-4-(3-trifluoromethylphenyl)-5-methylamino-2,3-dihydrofuran;

2-[1-methyl-2-(phenyl)ethyl]-3-oxo-4-(3-trifluoromethylphenyl)-5-methylamino-2,3-dihydrofuran;

2-naphth-1-ylmethylene-3-oxo-4-(3-trifluoromethylphenyl)-5-methylamino-2,3-dihydrofuran;

2-(2-fluoronaphth-1-ylmethylene)-3-oxo-4-(3-trifluoromethylphenyl)-5-methylamino-2,3-dihydrofuran;

2-(3-butylnaphth-1-ylmethylene)-3-oxo-4-(3-trifluoromethylphenyl)-5-methylamino-2,3-dihydrofuran;

2-(5-methoxynaphth-1-ylmethylene)-3-oxo-4-(3-trifluoromethylphenyl)-5-methylamino-2,3-dihydrofuran;

2-(6-nitronaphth-1-ylmethylene)-3-oxo-4-(3-trifluoromethylphenyl)-5-methylamino-2,3-dihydrofuran;

2-(7-trifluoromethylnaphth-1-ylmethylene)-3-oxo-4-(3-trifluoromethylphenyl)-5-methylamino-2,3-dihydrofuran;

2-(2-chloro-8-methylnaphth-1-ylmethylene)-3-oxo-4-(3-trifluoromethylphenyl)-5-methylamino-2,3-dihydrofuran;

2-(3-methoxy-5-nitro-7-fluoromethylnaphth-1-yl)-3-oxo-4-(3-trifluoromethylphenyl)-5-methylamino-2,3-dihydrofuran;

2-(beta-naphth-1-ylethyl)-3-oxo-4-(3-trifluoromethylphenyl)-5-methylamino-2,3-dihydrofuran;

2-[beta-(8-fluoronaphth-1-yl)ethyl]-3-oxo-4-(3-trifluoromethylphenyl)-5-methylamino-2,3-dihydrofuran;

2-[1-(7-methoxynaphth-1-yl)ethyl]-3-oxo-4-(3-trifluoromethylphenyl)-5-methylamino-2,3-dihydrofuran;

2-inden-1-ylmethylene-3-oxo-4-(3-trifluoromethylphenyl)-5-methylamino-2,3-dihydrofuran; and 2-(2-fluoroinden-1-ylmethylene)-3-oxo-4-(3-trifluoromethylphenyl)-5-methylamino-2,3-dihydrofuran.

Similarly, by approximately doubling the amount of dimethylsulfate and increasing the reaction time, the corresponding 5-dimethylamino homologs of the above compounds can be prepared. Similarly, by using diethylsulfate in place of dimethylsulphate the corresponding 5-ethylamino and 5-diethylamino homologs of the above compounds can be prepared.

EXAMPLE 8

2-(2-Fluorophenyl)-3-oxo-4-(3-trifluoromethylphenyl)-5-allylamino-2,3-dihydrofuran One gram of sodium hydroxide in 4.0 ml of water was added to a mixture of 4.0 g of 2-(2-fluorophenyl)-3-oxo-4-(3-trifluoromethylphenyl)-5-amino-2,3-dihydrofuran in 80 ml of methylene chloride at room temperature followed by the addition of 1.44 g of allyl bromide and 0.27 g of benzyltriethylammonium chloride. The resulting two-phase mixture was stirred at room temperature for about 18 hours after which time it was washed three times with water, dried over magnesium sulfate and concentrated in vacuo. The residue was purified by chromatography over silica gel eluting with chloroform to yield 2.5 g of the title compound.

Similarly, by applying this procedure to the products listed in Examples 2, 3 and 6, the corresponding 5-allylamino analogs thereof can be prepared. Similarly, by approximately doubling the amount of allyl bromide and sodium hydroxide, the corresponding 5-diallylamino analogs thereof can be prepared.

In a like manner, by using ethyl bromide in place of allyl bromide, the corresponding 5-ethylamino and 5-diethylamino analogs can be prepared.

Similarly, by following the same procedure by respectively using methoxymethyl bromide, ethylthiomethyl bromide, methyl bromoacetate, methyl 2-bromobutyrate, 1,5-dibromopentane, and cis-1,4-dibromobut-1,3-diene in place of alkyl bromide the corresponding 5-methoxymethylamino, 5-ethylthiomethylamino, 5-methoxycarbonylmethylamino, 5-(1-methoxycarbonylpropylamino), 5-piperidin-1-yl and 5-pyrrol-1-yl analogs of the products listed in Examples 2, 3 and 6 can be prepared for example:

2-phenyl-3-oxo-4-(3-trifluoromethylphenyl)-5-methoxymethylamino-2,3-dihydrofuran;

2-methyl-3-oxo-4-(3-trifluoromethylphenyl)-5-methoxymethylamino-2,3-dihydrofuran;

2-ethyl-3-oxo-4-(3-trifluoromethylphenyl)-5-methoxymethylamino-2,3-dihydrofuran;

2-phenyl-3-oxo-4-(3-trifluoromethylphenyl)-5-ethylthiomethylamino-2,3-dihydrofuran;

2-methoxy-3-oxo-4-(3-trifluoromethylphenyl)-5-ethylthiomethylamino-2,3-dihydrofuran;

2-methyl-3-oxo-4-(3-trifluoromethylphenyl)-5-ethylthiomethylamino-2,3-dihydrofuran;

2-ethoxymethylene-3-oxo-4-(3-trifluoromethylphenyl)-5-ethylthiomethylamino-2,3-dihydrofuran;

2-ethyl-3-oxo-4-(3-trifluoromethylphenyl)-5-ethylthiomethylamino-2,3-dihydrofuran;

2-phenyl-3-oxo-4-(3-trifluoromethylphenyl)-5-methoxycarbonylmethylamino-2,3-dihydrofuran;

2-methyl-3-oxo-4-(3-trifluoromethylphenyl)-5-methoxycarbonylmethylamino-2,3-dihydrofuran;

2-methylthiomethylene-3-oxo-4-(3-trifluoromethylphenyl)-5-methoxycarbonylmethylamino-2,3-dihydrofuran;

2-ethyl-3-oxo-4-(3-trifluoromethylphenyl)-5-methoxycarbonylmethylamino-2,3-dihydrofuran;

2-phenyl-3-oxo-4-(3-trifluoromethylphenyl)-5-(1-methoxycarbonylprop-1-yl)amino-2,3-dihydrofuran;

2-methyl-3-oxo-4-(3-trifluoromethylphenyl)-5-(1-methoxycarbonylprop-1-yl)amino-2,3-dihydrofuran;

2-fluoro-3-oxo-4-(3-trifluoromethylphenyl)-5-(1-methoxycarbonylprop-1-yl)amino-2,3-dihydrofuran;

2-ethyl-3-oxo-4-(3-trifluoromethylphenyl)-5-(1-methoxycarbonylprop-1-yl)amino-2,3-dihydrofuran;

2-naphth-1-yl-3-oxo-4-(3-trifluoromethylphenyl)-5-(1-methoxycarbonylprop-1-yl)amino-2,3-dihydrofuran;

2-inden-1-yl-3-oxo-4-(3-trifluoromethylphenyl)-5-(1-methoxycarbonylprop-1-yl)amino-2,3-dihydrofuran, 2-phenyl-3-oxo-4-(3-trifluoromethylphenyl)-5-piperidin-1-yl-2,3-dihydrofuran; and 2-phenyl-3-oxo-4-(3-trifluoromethylphenyl)-5-pyrrol-1-yl-2,3-dihydrofuran, etc.

Similarly, by applying the above procedures using the 5-methylamino products of Example 7 as starting materials, the corresponding 5-(N-methyl-N-allylamino), 5-(N-methyl-N-ethylamino), 5-(N-methyl-N-methoxymethylamino), 5-(N-methyl-N-ethylthiomethylamino), 5-(N-methyl-N-methoxycarbonylmethylamino), and 5-(N-methyl-N-1'-methoxycarbonylpropylamino) analogs can be prepared.

EXAMPLE 9

Lithium salt of 2-phenyl-3-oxo-4-(3-trifluoromethylphenyl)-5-methylamino-2,3-dihydrofuran ($R^1$=—$CH_3$, $R^2$=Li)

In this example, 5.4 ml of 1.6M n-butyllithium in hexane was added dropwise to a stirred solution containing 2.86 g of 2-phenyl-3-oxo-4-(3-trifluoromethylphenyl)-5-methylamino-2,3-dihydrofuran in 25 ml of tetrahydrofuran at −30° C. The resulting mixture was stirred for 20 minutes and then concentrated in vacuo affording 2.8 g of the title compound as a light brown solid. Elemental analysis: calculated, C-63.74, H-3.84, N-4.13; found, C-61.82, H-4.90, N-3.48.

Similarly, by adapting the above procedure, the corresponding lithium salts of the compounds of Examples 2, 3 and 6–8 can also be prepared.

EXAMPLE 10

Hydrobromide addition salt of 2-phenyl-3-oxo-4-(3-trifluoromethyl-phenyl)-5-amino-2,3-dihydrofuran In this example gaseous hydrogen bromide was bubbled into a slurry containing 2.25 g (0.007 mole) of 2-phenyl-3-oxo-4-(3-trifluoromethylphenyl)-5-amino-2,3-dihydrofuran in 35 ml of methylene chloride at room temperature. The addition of hydrogen bromide was discontinued when the solution cleared. The solution was evaporated to dryness affording 2.83 g of the title compound as the residue.

Similarly, by adapting the above procedure the corresponding hydrobromide addition salts of the compounds of Examples 2, 3 and 6 can be prepared.

EXAMPLE 11

The compounds listed in the tables hereinbelow were prepared using the appropriate starting materials and the appropriate procedures described hereinabove.

TABLE A

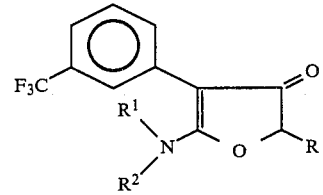

| No. | $R^1$ | $R^2$ | R | Carbon Calc. | Carbon Found | Hydrogen Calc. | Hydrogen Found | Nitrogen Calc. | Nitrogen Found | Melting Point °C. |
|---|---|---|---|---|---|---|---|---|---|---|
| 1 | H | H | ø** | 63.95 | 64.66 | 3.76 | 4.19 | 4.39 | 4.78 | 182–184* |
| 2 | $CH_3$ | H | ø | 64.86 | 64.22 | 4.20 | 4.65 | 4.20 | 3.79 | 154–155 |
| 3 | $CH_3$ | $CH_3$ | ø | 65.71 | 65.63 | 4.61 | 4.83 | 4.03 | 4.12 | 102–106 |
| 4 | $CH_2CH_3$ | H | ø | 65.71 | 66.55 | 4.61 | 5.12 | 4.03 | 3.98 | 143–145 |
| 5 | $CH_2CH_3$ | $CH_2CH_3$ | ø | 67.20 | 67.76 | 5.33 | 5.63 | 3.73 | 3.77 | 115–120 |
| 6 | H | H | 4-Fø | 60.53 | 59.66 | 3.26 | 3.47 | 4.15 | 4.12 | 136–138 |
| 7 | $CH_3$ | H | 2-Fø | 61.54 | 61.22 | 3.70 | 3.62 | 3.99 | 4.45 | 151–156 |
| 8 | $CH_3$ | $CH_3$ | 2-Fø | 62.47 | 62.95 | 4.11 | 4.38 | 3.84 | 4.08 | 91–93 |
| 9 | $CH_2CH_3$ | H | 2-Fø | 62.47 | 60.36 | 4.11 | 4.11 | 3.84 | 4.02 | 136–138 |
| 10 | $(CH_2)_2CH_3$ | H | 2-Fø | 63.32 | 63.6 | 4.49 | 4.7 | 3.69 | 3.71 | 53–60 |
| 11 | $CH_2CH_3$ | $CH_2CH_3$ | 2-Fø | 64.12 | 63.41 | 4.83 | 4.93 | 3.56 | 3.85 | oil |
| 12 | $CH_3$ | H | 2-Clø | 58.78 | 58.52 | 3.54 | 3.63 | 3.81 | 4.05 | 201–204* |
| 13 | $CH_3$ | $CH_3$ | 2-Clø* | 59.77 | 59.67 | 3.93 | 4.05 | 3.67 | 3.72 | 116–119 |
| 14 | $CH_2CH_3$ | H | 2-Clø | 59.77 | 60.5 | 3.93 | 4.05 | 3.67 | 3.89 | 131–137 |
| 15 | $CH_2CH_3$ | $CH_2CH_3$ | 2-Clø | 61.55 | 61.72 | 4.64 | 4.79 | 3.42 | 3.77 | 113–114 |
| 16 | H | H | 2-$CH_3$ø | 64.86 | 65.02 | 4.20 | 4.43 | 4.20 | 4.28 | 179–181* |
| 17 | H | H | 3-$CH_3$ø | 64.86 | 62.54 | 4.20 | 4.27 | 4.20 | 3.82 | 148–151 |
| 18 | H | H | 4-$CH_3$ø | 64.86 | 65.86 | 4.20 | 4.25 | 4.20 | 4.34 | 208–211* |
| 19 | H | H | 2-$CF_3$ø | 55.81 | 55.58 | 2.84 | 3.05 | 3.62 | 3.69 | 68–75 |
| 20 | H | H | 3-$CF_3$ø | 55.81 | 55.37 | 2.84 | 3.09 | 3.62 | 3.40 | 60–63 |
| 21 | H | H | 2,6-diFø | 57.46 | 57.45 | 2.82 | 3.14 | 3.94 | 4.16 | 225–227* |
| 22 | $CH_3$ | H | 2,6-diFø | 58.54 | 59.3 | 3.25 | 3.45 | 3.79 | 3.84 | 191–193* |
| 23 | $CH_2CH_3$ | H | 2,6-diFø | 59.53 | 60.11 | 3.66 | 4.00 | 3.66 | 3.71 | 63–65 |
| 24 | —$CH_2CH=CH_2$ | H | 2-Fø | 63.66 | 62.4 | 3.98 | 4.31 | 3.71 | 4.27 | oil |
| 25 | H | H | $CH_3$ | 56.03 | 56.54 | 3.89 | 4.22 | 5.45 | 5.52 | 129–130 |
| 26 | —$CH_2C(Cl)=CH_2$ | H | ø | 61.0 | 57.9 | 3.8 | 3.9 | 3.55 | 3.2 | oil |
| 27 | —$CH_2CH=C(Cl)CH_3$ | H | ø | 61.8 | 61.3 | 4.2 | 4.7 | 3.4 | 3.1 | 134–138 |
| 28 | —$CH(CH_3)COOC_2H_5$ | H | ø | 63.0 | 61.5 | 4.8 | 5.0 | 3.3 | 3.2 | oil |
| 29 | Li | —$CH_3$ | ø | 63.74 | 61.82 | 3.84 | 4.9 | 4.13 | 3.48 | 120* |
| 30 | H | H | 1-naphthyl | 68.3 | 65.8 | 3.8 | 4.1 | 3.8 | 3.8 | 123–126 |
| 31 | $CH_3$ | H | 1-naphthyl | 68.9 | 65.7 | 4.18 | 4.4 | 3.7 | 3.55 | 174–179 |
| 32 | $CH_3$ | $CH_3$ | 1-naphthyl | 69.5 | 69.2 | 4.5 | 4.7 | 3.5 | 3.6 | 139–143 |
| 33 | H | H | H | 54.32 | 54.91 | 3.29 | 3.54 | 5.76 | 5.42 | 145–146* |
| 34 | $CH_3$ | H | H | 56.03 | 55.75 | 3.89 | 4.04 | 5.45 | 5.39 | 158–159 |
| 35 | $CH_3$ | H | $CH_3$ | 57.56 | 58.87 | 4.43 | 4.66 | 5.17 | 5.32 | 116–118 |
| 36 | $CH_2CH_3$ | H | $CH_3$ | 58.95 | 59.35 | 4.91 | 5.04 | 4.91 | 5.34 | 141–142 |
| 37 | H | H | $CH_2CH_3$ | 57.56 | 60.08 | 4.43 | 4.91 | 5.17 | 5.47 | 173–174 |
| 38 | $CH_3$ | H | $CH_2CH_3$ | 58.95 | 59.59 | 4.91 | 5.12 | 4.91 | 5.17 | 138–139 |
| 39 | H | H | $(CH_2)_2CH_3$ | 58.95 | 60.26 | 4.91 | 5.19 | 4.91 | 5.08 | 165–168 |
| 40 | $CH_3$ | H | $(CH_2)_2CH_3$ | 60.20 | 61.2 | 5.35 | 5.84 | 4.68 | 4.56 | oil |
| 41 | $CH_3$ | $CH_3$ | $(CH_2)_2CH_3$ | 61.34 | 61.82 | 5.75 | 6.11 | 4.47 | 4.46 | oil |

TABLE A-continued

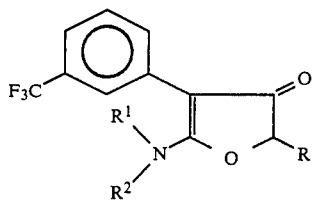

| No. | R¹ | R² | R | ELEMENTAL ANALYSIS Carbon Calc. | Found | Hydrogen Calc. | Found | Nitrogen Calc. | Found | Melting Point °C. |
|---|---|---|---|---|---|---|---|---|---|---|
| 42 | H | H | CH(CH₃)₂ | 58.95 | 58.79 | 4.91 | 5.23 | 4.91 | 5.0 | 155–156 |
| 43 | CH₃ | H | CH(CH₃)₂ | 60.20 | 60.80 | 5.35 | 5.36 | 4.68 | 4.85 | 121–122 |
| 44 | H | H | (CH₂)₃CH₃ | 60.20 | 61.42 | 5.35 | 5.68 | 4.68 | 4.9 | 137–138* |
| 45 | CH₃ | H | (CH₂)₃CH₃ | 61.34 | 62.84 | 5.75 | 6.17 | 4.47 | 5.03 | 90 |
| 46 | CH₃ | H | cyclohexyl | 63.72 | 64.41 | 5.90 | 6.18 | 4.13 | 3.6 | 143–145 |
| 47 | CH₂CH₃ | H | cyclohexyl | 64.59 | 64.94 | 6.23 | 6.87 | 3.97 | 4.11 | 142–143 |

\* = Decomposition
ø\* = Phenyl, for example, 2,6-diFø = 2,6-difluorophenyl
ø\*\* = Phenyl, for example, 2-Clø = 2-chlorophenyl

TABLE B

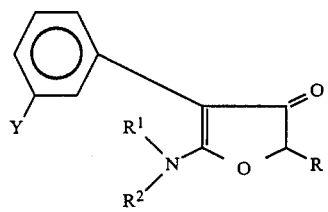

| No. | R¹ | R² | R | Y | Carbon Calc. | Found | Hydrogen Calc. | Found | Nitrogen Calc. | Found | Melting Point °C. |
|---|---|---|---|---|---|---|---|---|---|---|---|
| 48 | H | H | 2-CH₃ø | Cl | 68.11 | 68.64 | 4.67 | 4.97 | 4.67 | 4.96 | 175–177 |
| 49 | H | H | 2-Fø | Cl | 63.26 | 62.3 | 3.62 | 3.8 | 4.61 | 4.17 | 178–180* |
| 50 | CH₃ | H | 2-Clø | Cl | 61.08 | 62.21 | 3.87 | 4.06 | 4.19 | 4.33 | 185–193* |
| 51 | CH₃ | H | H | Cl | 59.07 | 59.1 | 4.48 | 4.95 | 6.27 | 6.24 | 117–120* |
| 52 | CH₂CH₃ | H | H | Cl | 60.64 | 61.11 | 5.05 | 5.52 | 5.90 | 6.03 | 117–178 |
| 53 | H | H | CH₃ | Cl | 59.07 | 57.16 | 4.48 | 4.5 | 6.27 | 5.73 | 158–159 |
| 54 | CH₃ | H | CH₃ | Cl | 66.64 | 62.11 | 5.05 | 5.42 | 5.90 | 6.05 | 119–122 |
| 55 | H | H | CH₂CH₃ | Cl | 60.64 | 58.59 | 5.09 | 5.46 | 5.89 | 5.67 | 152–155 |
| 56 | CH₃ | H | CH₂CH₃ | Cl | 62.03 | 63.34 | 5.61 | 5.83 | 5.56 | 5.96 | 95–97 |
| 57 | CH₃ | CH₃ | CH₂CH₃ | Cl | 63.28 | 62.48 | 6.07 | 6.86 | 5.27 | 5.93 | oil |
| 58 | CH₂CH₂ | H | CH₂CH₃ | Cl | 63.28 | 63.82 | 6.7 | 6.52 | 5.27 | 5.89 | 120–123 |
| 59 | H | H | (CH₂)₂CH₃ | Cl | 62.03 | 62.13 | 5.61 | 5.76 | 5.56 | 5.63 | 152–154 |
| 60 | CH₃ | H | (CH₂)₂CH₃ | Cl | 63.28 | 63.58 | 6.07 | 6.49 | 5.27 | 5.86 | oil |
| 61 | CH₂CH₃ | H | (CH₂)₂CH₃ | Cl | 64.40 | 65.34 | 6.49 | 7.11 | 5.01 | 5.33 | 104–106 |
| 62 | CH₃ | CH₃ | (CH₂)₂CH₃ | Cl | 64.40 | 64.14 | 6.49 | 6.65 | 5.01 | 4.67 | oil |
| 63 | H | H | CH₂(CH₃)₂ | Cl | 62.04 | 63.69 | 5.57 | 6.05 | 5.57 | 6.37 | 156–157 |
| 64 | CH₃ | H | CH₂(CH₃)₂ | Cl | 63.29 | 63.03 | 6.03 | 6.72 | 5.27 | 5.62 | 85–91 |
| 65 | CH₂CH₃ | H | CH₂(CH₃)₂ | Cl | 64.41 | 65.66 | 6.44 | 6.83 | 5.01 | 5.47 | 130–131 |
| 66 | H | H | ø | Br | 58.20 | 54.8 | 3.64 | 3.79 | 4.24 | 3.97 | 177–178* |
| 67 | CH₃ | H | ø | Br | 59.32 | 60.79 | 4.07 | 4.36 | 4.07 | 3.93 | 181–185 |
| 68 | CH₂CH₃ | H | ø | Br | 60.35 | 61.01 | 4.47 | 4.74 | 3.91 | 3.53 | 161–163 |
| 69 | H | H | 2-Clø | Br | 52.69 | 54.59 | 3.02 | 3.26 | 3.84 | 4.14 | 202–204 |
| 70 | CH₃ | H | 2-Clø | Br | 53.91 | 53.77 | 3.44 | 3.47 | 3.70 | 3.69 | 205–207 |
| 71 | CH₂CH₃ | H | 2-Clø | Br | 55.05 | 55.3 | 3.82 | 3.97 | 3.57 | 3.51 | 144–147 |
| 72 | H | H | 2-Fø | Br | 55.19 | 55.14 | 3.16 | 3.57 | 4.02 | 3.94 | 190–191.5 |
| 73 | CH₃ | H | 2-Fø | Br | 56.37 | 58.0 | 3.59 | 3.41 | 3.87 | 4.51 | 172–173 |
| 74 | CH₂CH₃ | H | 2-Fø | Br | 57.46 | 57.59 | 3.99 | 4.31 | 3.72 | 3.57 | 157–159 |
| 75 | H | H | 2-CH₃ø | Br | 59.32 | 58.48 | 4.07 | 4.22 | 4.07 | 4.03 | 165–167 |
| 76 | CH₃ | H | 2-CH₃ø | Br | 60.35 | 60.36 | 4.47 | 4.68 | 3.91 | 3.96 | 208–210 |
| 77 | CH₂CH₃ | H | 2-CH₃ø | Br | 61.31 | 62.98 | 4.84 | 5.16 | 3.76 | 4.24 | 140–142 |
| 78 | CH₃ | H | H | Br | 49.21 | 48.01 | 3.73 | 4.41 | 5.23 | 5.06 | 109–118 |
| 79 | CH₂CH₃ | H | H | Br | 51.08 | 50.35 | 4.26 | 4.28 | 4.97 | 4.86 | 172–175* |
| 80 | H | H | ø | CH₃ | 77.0 | 76.3 | 5.7 | 5.9 | 5.3 | 5.1 | 137–141 |
| 81 | CH₃ | H | ø | CH₃ | 77.4 | 77.1 | 6.1 | 6.4 | 5.0 | 5.1 | 150–152 |
| 82 | H | H | ø | OCH₃ | 72.6 | 73.7 | 5.4 | 6.6 | 5.0 | 5.1 | 141–144 |
| 83 | CH₃ | H | ø | OCH₃ | 73.2 | 72.5 | 5.8 | 5.9 | 4.7 | 3.6 | 128–133 |
| 84 | CH₃ | H | ø | OCH(CH₃)₂ | 74.30 | 70.02 | 6.5 | 6.47 | 4.33 | 4.21 | 185–188* |
| 85 | CH₂CH₃ | H | ø | OCH(CH₃)₂ | 74.25 | 75.88 | 6.87 | 7.23 | 4.15 | 4.23 | 111–113 |
| 86 | H | H | 2-CH₃ø | OCH(CH₃)₂ | 74.28 | 73.58 | 6.55 | 6.85 | 4.33 | 4.17 | 149–151 |
| 87 | CH₃ | H | 2-CH₃ø | OCH(CH₃)₂ | 74.75 | 74.35 | 6.82 | 6.95 | 4.15 | 3.83 | 134–135 |

TABLE B-continued

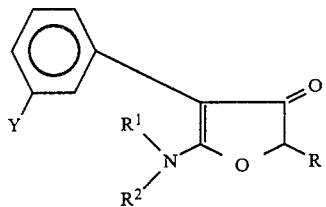

| No. | R¹ | R² | R | Y | Carbon Calc. | Carbon Found | Hydrogen Calc. | Hydrogen Found | Nitrogen Calc. | Nitrogen Found | Melting Point °C. |
|---|---|---|---|---|---|---|---|---|---|---|---|
| 88 | CH₂CH₃ | H | 2-CH₃∅ | OCH(CH₃)₂ | 75.19 | 73.63 | 7.17 | 7.27 | 3.99 | 4.19 | 134–136 |
| 89 | H | H | 2-F∅ | OCH(CH₃)₂ | 69.71 | 70.7 | 5.54 | 5.74 | 4.28 | 4.25 | 150–151 |
| 90 | CH₃ | H | 2-F∅ | OCH(CH₃)₂ | 70.37 | 69.66 | 5.91 | 6.1 | 4.10 | 4.25 | 191–193 |
| 91 | H | H | 2-Cl∅ | OCH(CH₃)₂ | 66.38 | 68.29 | 4.07 | 4.36 | 5.28 | 5.48 | 171–173 |
| 92 | H | H | CH₃ | OCH(CH₃)₂ | 68.0 | 65.75 | 6.9 | 6.6 | 5.7 | 5.6 | 151–155 |
| 93 | CH₃ | H | CH₃ | OCH(CH₃)₂ | 68.97 | 68.69 | 7.28 | 8.01 | 5.36 | 6.15 | 114–115 |
| 94 | H | H | ∅ | —O∅ | 76.95 | 76.3 | 5.0 | 6.0 | 4.1 | 3.0 | 73–78 |
| 95 | CH₃ | H | ∅ | —O∅ | 77.3 | 73.9 | 5.3 | 5.6 | 3.9 | 4.1 | 163–167 |
| 96¹ | CH₃ | CH₃ | ∅ | Y = Cl, C = Cl | 62.1 | 62.9 | 4.3 | 4.7 | 4.0 | 4.0 | 133–137 |
| 97 | —CH₂(—CH₂)₂—CH₂— | | ∅ | ∅ —CF₃ | 67.55 | 72.4 | 4.85 | 5.1 | 3.75 | 3.8 | 105–111 |

96¹ is 2-phenyl-3-oxo-4-(3,4-dichlorophenyl)-5-dimethylamino-2,3-dihydrofuran
* = Decomposition

TABLE C
COMPARISON COMPOUNDS

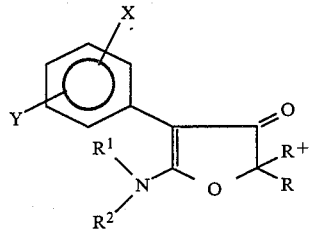

(unless otherwise noted X = H and R⁺ = H)

| No. | R¹ | R² | R | Y | Carbon Calc. | Carbon Found | Hydrogen Calc. | Hydrogen Found | Nitrogen Calc. | Nitrogen Found | Melting Point °C. |
|---|---|---|---|---|---|---|---|---|---|---|---|
| C-1 | CH₃ | CH₃ | ∅ | H | 77.42 | 75.64 | 6.09 | 6.39 | 5.02 | 5.03 | 111–115 |
| C-2 | H | H | H | H | 68.57 | 68.99 | 5.14 | 5.78 | 8.0 | 7.87 | 221–223* |
| C-3 | H | H | H | 3-Cl | 57.29 | 51.6 | 6.68 | 5.67 | 3.82 | 3.7 | 214–216* |
| C-4 | H | H | H | 4-Cl | 57.29 | 53.46 | 6.68 | 5.52 | 3.82 | 4.11 | 169–170* |
| C-5 | CH₃ | H | H | 4-Cl | 59.07 | 59.34 | 4.48 | 5.03 | 6.27 | 6.02 | 133–137* |
| C-6 | CH₃ | CH₃ | H | 4-Cl | 60.64 | 58.61 | 5.05 | 5.24 | 5.90 | 5.76 | 161–163 |
| C-7 | CH₃ | H | ∅ | 4-Cl | 68.1 | 64.4 | 4.7 | 5.3 | 4.7 | 4.5 | oil |
| C-8 | H | H | H | 4-CH₃ | 69.84 | 67.98 | 5.82 | 5.63 | 7.41 | 6.7 | 189–191* |
| C-9 | CH₃ | H | H | 4-CH₃ | 70.94 | 70.85 | 6.4 | 6.63 | 6.9 | 6.96 | 151–156* |
| C-10 | H | H | ∅ | 4-CH₃ | 77.0 | 76.2 | 5.7 | 5.9 | 5.3 | 5.05 | 142–146 |
| C-11 | CH₃ | H | ∅ | 4-CH₃ | 77.4 | 75.49 | 6.1 | 6.14 | 5.0 | 4.89 | 148–154 |
| C-12 | H | H | ∅ | 4-OCH₃ | 72.6 | 70.5 | 5.4 | 6.0 | 5.0 | 4.8 | 138–141 |
| C-13 | CH₃ | CH₃ | ∅ | 4-OCH₃ | 73.8 | 72.9 | 6.2 | 6.7 | 4.5 | 4.7 | 140–143 |
| C-14 | ** | H | ∅ | 3-CF₃ | 62.7 | 62.4 | 3.4 | 4.5 | 6.35 | 5.8 | oil |
| C-15 | CH₃ | CH₃ | R = ∅, R⁺ = Cl | 3-CF₃ | 59.76 | 57.9 | 3.93 | 4.06 | 3.67 | 3.56 | oil |
| C-16² | H | H | ∅ | Y = 3-Cl, X = 4-Cl | 60.0 | 60.1 | 3.5 | 3.7 | 4.4 | 4.8 | 179–182 |

C-16² is 2-phenyl-3-oxo-4-(3,4-dichlorophenyl)-5-amino-2,3-dihydrofuran
* = Decomposition
** = 4-NO₂∅—

EXAMPLE 12

In this example, the compounds of Example 11 were respectively tested using the procedures described hereinbelow for pre-emergent and post-emergent activity against a variety of grasses and broad-leaf plants including one grain crop and one broad-leaf crop. The compounds tested are identified by compound number in Example 11 hereinabove.

PRE-EMERGENT HERBICIDE TEST

Pre-emergence herbicidal activity was determined in the following manner.

Test solutions of the respective compounds were prepared as follows:

355.5 mg of test compound was dissolved in 15 ml of acetone. 2 ml of acetone containing 110 mg of a nonionic surfactant was added to the solution. 12 ml of this stock solution was then added to 47.7 ml of water which contained the same nonionic surfactant at a concentration of 625 mg/l.

Seeds of the test vegetation were planted in a pot of soil and the test solution was sprayed uniformly onto the soil surface either at a dose of 27.5 micrograms/cm$^2$ or in some instances as indicated in Table 1 hereinbelow, certain of the compounds were tested at a lower dosage of 15.6 micrograms/cm$^2$. The pot was watered and placed in a greenhouse. The pot was watered intermittently and observed for seedling emergence, health of emerging seedlings, etc., for a 3-week period. At the end of this period, the herbicidal effectiveness of the compound was rated based on the physiological observations. A 0-to-100 scale was used, 0 representing no phytotoxicity, 100 representing complete kill. The results of these tests are summarized in Table 1.

POST-EMERGENT HERBICIDAL TEST

The test compound was formulated in the same manner as described above for the pre-emergent test. This formulation was uniformly sprayed on 2 similar pots containing plants 2 to 3 inches tall (except wild oats, soybean and watergrass which were 3 to 4 inches tall) (approximately 15 to 25 plants per pot) at a dose of 27.5 microgram/cm$^2$. After the plants had dried, they were placed in a greenhouse and then watered intermittently at their bases as needed. The plants were observed periodically for phytotoxic effects and physiological and morphological responses to the treatment. After 3 weeks, the herbicidal effectiveness of the compound was rated based on these observations. A 0-to-100 scale was used, 0 representing no phytotoxicity, 100 representing complete kill. The results of these tests are summarized in Table 2.

TABLE 1

Pre-Emergence Herbicidal Activity
Application Rate: 27.5 micrograms/cm$^2$, unless otherwise noted

| Compound No. | Broad-Leaf Plants % Phytotoxicity | | | | Grasses % Phytotoxicity | | | |
|---|---|---|---|---|---|---|---|---|
| | Lambsquarter | Mustard | Pigweed | Soybean | Crabgrass | Watergrass | Wild Oats | Rice |
| 1 | 94 | 100 | 100 | 95 | 100 | 100 | 100 | 93 |
| 2 | 100 | 100 | 100 | 100 | 100 | 100 | 100 | 100 |
| 3[a] | 98 | 100 | 100 | 60 | 100 | 80 | 100 | 60 |
| 4[a] | 95 | 100 | 100 | 98 | 100 | 100 | 100 | 75 |
| 5 | 100 | 80 | 100 | 20 | 100 | 70 | 100 | 20 |
| 6 | 100 | 100 | 100 | 85 | 100 | 100 | 100 | 85 |
| 7[a] | 100 | 100 | 100 | 100 | 100 | 100 | 100 | 100 |
| 8[a] | 98 | 100 | 100 | 100 | 100 | 100 | 100 | 70 |
| 9[a] | 100 | 100 | 100 | 100 | 100 | 100 | 100 | 100 |
| 10 | 100 | 100 | 100 | 90 | 100 | 100 | 100 | 90 |
| 11[a] | 90 | 50 | 100 | 60 | 100 | 50 | 60 | 20 |
| 12[a] | 100 | 100 | 100 | 90 | 100 | 100 | 100 | 95 |
| [11] 13[a] | 100 | 100 | 100 | 100 | 100 | 100 | 100 | 95 |
| 14[a] | 100 | 100 | 100 | 70 | 100 | 100 | 100 | 95 |
| [11] 15[a] | 95 | 90 | 100 | 20 | 100 | 50 | 70 | 0 |
| 16 | 100 | 100 | 100 | 85 | 100 | 100 | 100 | 95 |
| 17 | 99 | 83 | 98 | 55 | 100 | 70 | 63 | 55 |
| 18 | 0 | 0 | 0 | 0 | 0 | 0 | 0 | 0 |
| 19[a] | 100 | 80 | 100 | 20 | 98 | 100 | 100 | 90 |
| 20 | 100 | 100 | 100 | 75 | 98 | 65 | 85 | 50 |
| 21 | 95 | 90 | 25 | 40 | 100 | 100 | 100 | 80 |
| 22 | 100 | 100 | 100 | 100 | 100 | 100 | 100 | 100 |
| 23 | 100 | 100 | 100 | 70 | 100 | 100 | 100 | 95 |
| 24[a] | 98 | 90 | 100 | 65 | 100 | 95 | 70 | 55 |
| 25 | 90 | 98 | 85 | 90 | 100 | 88 | 80 | 65 |
| 26 | 95 | 75 | 100 | 30 | 0 | 95 | 0 | 30 |
| 27 | 0 | 0 | 0 | 0 | 0 | 0 | 0 | 0 |
| 28 | 99 | 98 | 100 | 45 | 99 | 48 | 67 | 45 |
| 29 | 98 | 97 | 100 | 98 | 100 | 100 | 90 | 100 |
| 30 | 98 | 55 | 100 | 25 | 78 | 55 | 55 | 15 |
| 31 | 100 | 100 | 100 | 80 | 100 | 100 | 95 | 80 |
| 32 | 95 | 80 | 100 | 25 | 100 | 80 | 60 | 75 |
| 33 | 95 | 100 | 70 | 78 | 98 | 80 | 90 | 78 |
| 34 | 100 | 100 | 100 | 100 | 100 | 100 | 100 | 100 |
| 35 | 100 | 100 | 100 | 100 | 100 | 100 | 100 | 100 |
| 36 | 100 | 100 | 100 | 100 | 100 | 100 | 100 | 100 |
| 37 | 100 | 100 | 100 | 85 | 98 | 98 | 98 | 70 |
| 38 | 100 | 100 | 100 | 100 | 100 | 100 | 100 | 100 |
| 39 | 100 | 100 | 100 | 70 | 100 | 100 | 100 | 88 |
| 40 | 100 | 100 | 100 | 100 | 100 | 100 | 100 | 100 |
| 41 | 100 | 100 | 100 | 50 | 100 | 100 | 100 | 65 |
| 42 | 95 | 100 | 100 | 25 | 35 | 88 | 10 | 0 |
| 43 | 100 | 100 | 100 | 100 | 100 | 100 | 100 | 100 |
| 44 | 90 | 100 | 100 | 15 | 98 | 99 | 75 | 10 |
| 45 | 100 | 100 | 100 | 93 | 100 | 100 | 100 | 100 |
| 46 | 100 | 100 | 100 | 70 | 100 | 100 | 90 | 70 |
| 47 | 100 | 55 | 60 | 30 | 100 | 95 | 70 | |
| 48 | 60 | 65 | 30 | 75 | 25 | 25 | 25 | 93 |
| 49 | 100 | 100 | 100 | 100 | 100 | 100 | 100 | 100 |
| 50 | 100 | 100 | 100 | 100 | 100 | 100 | 100 | 100 |
| 51 | 100 | 100 | 100 | 98 | 100 | 100 | 100 | 95 |
| 52 | 100 | 100 | 100 | 100 | 100 | 100 | 100 | 100 |
| 53 | 60 | 65 | 50 | 35 | 0 | 15 | 0 | 0 |
| 54 | 100 | 100 | 100 | 93 | 100 | 100 | 100 | 97 |

TABLE 1-continued

Pre-Emergence Herbicidal Activity
Application Rate: 27.5 micrograms/cm², unless otherwise noted

| Compound No. | Broad-Leaf Plants % Phytotoxicity | | | | Grasses % Phytotoxicity | | | |
|---|---|---|---|---|---|---|---|---|
| | Lambsquarter | Mustard | Pigweed | Soybean | Crabgrass | Watergrass | Wild Oats | Rice |
| 55 | 55 | 50 | 0 | 25 | 73 | 20 | 0 | 0 |
| 56 | 100 | 100 | 100 | 100 | 100 | 100 | 100 | 80 |
| 57 | 98 | 100 | 100 | 45 | 100 | 65 | 30 | 40 |
| 58 | 100 | 100 | 75 | 90 | 100 | 100 | 85 | 90 |
| 59 | 50 | 45 | 0 | 0 | 60 | 15 | 0 | 0 |
| 60 | 100 | 100 | 100 | 99 | 100 | 100 | 100 | 97 |
| 61 | 100 | 100 | 85 | 93 | 100 | 100 | 80 | 93 |
| 62 | 100 | 100 | 100 | 45 | 100 | 94 | 50 | 30 |
| 63 | 25 | 45 | 0 | 0 | 20 | 20 | 0 | 0 |
| 64 | 98 | 100 | 100 | 93 | 100 | 100 | 95 | 60 |
| 65 | 100 | 100 | 100 | 90 | 100 | 100 | 100 | 85 |
| 66 | 100 | 100 | 100 | 70 | 100 | 95 | 98 | 90 |
| 67 | 100 | 100 | 100 | 100 | 100 | 100 | 100 | 100 |
| 68 | 100 | 100 | 100 | 100 | 100 | 100 | 100 | 100 |
| 69 | 100 | 98 | 99 | 75 | 100 | 100 | 99 | 85 |
| 70 | 100 | 95 | 90 | 90 | 100 | 100 | 100 | 95 |
| 71 | 100 | 95 | 97 | 70 | 100 | 100 | 95 | 93 |
| 72 | 100 | 100 | 99 | 85 | 100 | 100 | 100 | 99 |
| 73 | 100 | 100 | 100 | 100 | 100 | 100 | 93 | 100 |
| 74 | 100 | 100 | 80 | 93 | 100 | 100 | 98 | 97 |
| 75 | 100 | 99 | 100 | 50 | 100 | 100 | 98 | 95 |
| 76 | 100 | 93 | 85 | 90 | 100 | 100 | 99 | 93 |
| 77 | 100 | 99 | 98 | 85 | 100 | 100 | 94 | 93 |
| 78 | 100 | 98 | 70 | 90 | 100 | 100 | 100 | 98 |
| 79 | 100 | 100 | 100 | 100 | 100 | 100 | 100 | 100 |
| 80 | 25 | 20 | 0 | 0 | 95 | 25 | 10 | 0 |
| 81 | 100 | 100 | 100 | 100 | 100 | 100 | 100 | 0 |
| 82 | 80 | 55 | 20 | 45 | 98 | 25 | 20 | 0 |
| 83 | 100 | 100 | 100 | 70 | 100 | 100 | 100 | 0 |
| 84 | 99 | 95 | 100 | 98 | 100 | 100 | 100 | 97 |
| 85 | 100 | 97 | 100 | 97 | 100 | 100 | 99 | 97 |
| 86 | 100 | 100 | 100 | 85 | 100 | 100 | 90 | 75 |
| 87 | 100 | 95 | 100 | 95 | 99 | 100 | 98 | 80 |
| 88 | 100 | 100 | 100 | 90 | 100 | 100 | 98 | 90 |
| 89 | 100 | 100 | 100 | 99 | 100 | 100 | 100 | 100 |
| 90 | 100 | 100 | 100 | 100 | 100 | 100 | 99 | 99 |
| 91 | 99 | 100 | 100 | 97 | 100 | 100 | 95 | 97 |
| 92 | 20 | 20 | 0 | 25 | 0 | 0 | 0 | 0 |
| 93 | 100 | 100 | 100 | 100 | 100 | 100 | 100 | 93 |
| 94 | 75 | 55 | 98 | 0 | 90 | 30 | 0 | 0 |
| 95 | 100 | 100 | 100 | 55 | 100 | 100 | 75 | 40 |
| 96 | 93 | 50 | 100 | 0 | 100 | 60 | 30 | 0 |
| 97 | 100 | 100 | 100 | 70 | 100 | 100 | 99 | 80 |

$a$ = Tested at 15.6 micrograms/cm²

TABLE 1A

COMPARISON COMPOUNDS
Pre-Emergence Herbicidal Activity
Application Rate: 27.5 micrograms/cm², unless otherwise noted

| Compound No. | Broad-Leaf Plants % Phytotoxicity | | | | Grasses % Phytotoxicity | | | |
|---|---|---|---|---|---|---|---|---|
| | Lambsquarter | Mustard | Pigweed | Soybean | Crabgrass | Watergrass | Wild Oats | Rice |
| C-1 | 40 | 25 | 40 | 0 | 75 | 0 | 0 | 0 |
| C-2 | 0 | 0 | 0 | 0 | 0 | 0 | 0 | 0 |
| C-3 | 0 | 0 | 0 | 0 | 0 | 0 | 0 | 0 |
| C-4 | 0 | 0 | 0 | 0 | 0 | 0 | 0 | 0 |
| C-5 | 0 | 0 | 0 | 0 | 0 | 0 | 0 | 0 |
| C-6 | 0 | 0 | 0 | 0 | 0 | 0 | 0 | 0 |
| C-7 | 0 | 0 | 0 | 0 | 0 | 0 | 0 | 0 |
| C-8 | 30 | 25 | 0 | 40 | 0 | 0 | 0 | 0 |
| C-9 | 0 | 0 | 0 | 0 | 0 | 0 | 0 | 0 |
| C-10 | 0 | 0 | 0 | 0 | 0 | 0 | 0 | 0 |
| C-11 | 0 | 0 | 0 | 0 | 30 | 0 | 0 | 0 |
| C-12 | 0 | 0 | 0 | 0 | 0 | 0 | 0 | 0 |
| C-13 | 0 | 0 | 0 | 0 | 0 | 0 | 0 | 0 |
| C-14 | 0 | 0 | 0 | 0 | 45 | 35 | 0 | 0 |
| C-15 | 0 | 0 | 0 | 0 | 0 | 0 | 0 | 0 |
| C-16 | 0 | 0 | 0 | 0 | 0 | 0 | 0 | 0 |

TABLE 2

Post-Emergence Herbicidal Activity
Application Rate: 27.5 micrograms/cm², unless otherwise noted

| Compound No. | Broad-Leaf Plants % Phytotoxicity | | | | Grasses % Phytotoxicity | | | |
|---|---|---|---|---|---|---|---|---|
| | Lambsquarter | Mustard | Pigweed | Soybean | Crabgrass | Watergrass | Wild Oats | Rice |
| 1 | 60 | 100 | 50 | 50 | 40 | 33 | 45 | 20 |
| 2 | 85 | 100 | 92 | 90 | 58 | 60 | 60 | 42 |
| 3[a] | 70 | 90 | 75 | 65 | 0 | 0 | 0 | 0 |
| 4[a] | 60 | 95 | 75 | 80 | 50 | 65 | 65 | 45 |
| 5 | 80 | 90 | 70 | 60 | 30 | 30 | 30 | 0 |
| 6 | 60 | 80 | 60 | 40 | 45 | 60 | 60 | 20 |
| 7[a] | 95 | 100 | 98 | 100 | 80 | 80 | 90 | 80 |
| 8[a] | 65 | 100 | 64 | 80 | 40 | 65 | 65 | 20 |
| 9[a] | 80 | 95 | 90 | 90 | 70 | 90 | 90 | 60 |
| 10 | 90 | 100 | 90 | 80 | 30 | 0 | 30 | 0 |
| 11[a] | 90 | 90 | 90 | 80 | 30 | 20 | 20 | 20 |
| 12[a] | 100 | 100 | 90 | 90 | 90 | 40 | 50 | 20 |
| 13[a] | 90 | 100 | 90 | 90 | 30 | 50 | 0 | 0 |
| 14[a] | 80 | 90 | 90 | 70 | 50 | 80 | 90 | 40 |
| 15[a] | 80 | 90 | 80 | 70 | 20 | 0 | 0 | 0 |
| 16 | 65 | 95 | 60 | 55 | 70 | 80 | 75 | 20 |
| 17 | 35 | 73 | 35 | 30 | 0 | 0 | 0 | 0 |
| 18 | 0 | 0 | 0 | 0 | 0 | 0 | 0 | 0 |
| 19[a] | 55 | 45 | 45 | 0 | 55 | 45 | 40 | 0 |
| 20 | 43 | 80 | 45 | 33 | 0 | 0 | 0 | 0 |
| 21 | 50 | 30 | 60 | 50 | 30 | 0 | 0 | 0 |
| 22 | 80 | 80 | 70 | 70 | 60 | 90 | 70 | 0 |
| 23 | 85 | 100 | 90 | 80 | 70 | 100 | 60 | 30 |
| 24[a] | 85 | 80 | 75 | 65 | 40 | 35 | 0 | 0 |
| 25 | 25 | 50 | N.T.* | 50 | 0 | 0 | 0 | 0 |
| 26 | 40 | 55 | 60 | 45 | 0 | 0 | 0 | 0 |
| 27 | 50 | 30 | 35 | 0 | 0 | 0 | 0 | 0 |
| 28 | 35 | 40 | 0 | 0 | 0 | 0 | 0 | 0 |
| 29 | 75 | 100 | 100 | 80 | 70 | 85 | 65 | 52 |
| 30 | 30 | 45 | 45 | 45 | 10 | 30 | 20 | 0 |
| 31 | 70 | 80 | 80 | 70 | 30 | 40 | 20 | 0 |
| 32 | 40 | 40 | 35 | 35 | 0 | 0 | 0 | 0 |
| 33 | 70 | 65 | 42 | 50 | 35 | 40 | 60 | 45 |
| 34 | 85 | 100 | 85 | 85 | 80 | 92 | 89 | 60 |
| 35 | 100 | 100 | 100 | 100 | 100 | 90 | 98 | 75 |
| 36 | 75 | 98 | 70 | 70 | 65 | 80 | 65 | 35 |
| 37 | 50 | 50 | 45 | 40 | 0 | 0 | 0 | 0 |
| 38 | 85 | 100 | 100 | 70 | 75 | 75 | 75 | 65 |
| 39 | 47 | 60 | 40 | 0 | 0 | 0 | 0 | 0 |
| 40 | 95 | 100 | 98 | 80 | 95 | 95 | 95 | 95 |
| 41 | 90 | 100 | 90 | 90 | 45 | 75 | 75 | 30 |
| 42 | 11 | 0 | 10 | 25 | 0 | 0 | 0 | 0 |
| 43 | 80 | 100 | 75 | 95 | 90 | 80 | 90 | 45 |
| 44 | 25 | 25 | 25 | 20 | 0 | 0 | 0 | 0 |
| 45 | 75 | 95 | 90 | 90 | 55 | 75 | 65 | 0 |
| 46 | 50 | 50 | 50 | 40 | 20 | 25 | 0 | 0 |
| 47 | 70 | 70 | 70 | 85 | 40 | 30 | 35 | 15 |
| 48 | 60 | 65 | 30 | 30 | 25 | 25 | 25 | 0 |
| 49 | 75 | 90 | 80 | 40 | 60 | 60 | 30 | 75 |
| 50 | 85 | 90 | 90 | 65 | 80 | 85 | 80 | 55 |
| 51 | 50 | 50 | 40 | 60 | 30 | 25 | 25 | 0 |
| 52 | 95 | 100 | 95 | 85 | 60 | 60 | 75 | 25 |
| 53 | 30 | 15 | 0 | 33 | 0 | 0 | 0 | 0 |
| 54 | 60 | 87 | 75 | 73 | 35 | 40 | 0 | 0 |
| 55 | 0 | 0 | 0 | 0 | 0 | 0 | 0 | 0 |
| 56 | 55 | 93 | 70 | 90 | 0 | 0 | 0 | 0 |
| 57 | 30 | 45 | 85 | 70 | 0 | 0 | 0 | 0 |
| 58 | 45 | 50 | 30 | 65 | 0 | 0 | 0 | 0 |
| 59 | 0 | 0 | 0 | 0 | 0 | 0 | 0 | 0 |
| 60 | 75 | 98 | 80 | 80 | 20 | 20 | 0 | 0 |
| 61 | 75 | 85 | 80 | 90 | 30 | 25 | 10 | 10 |
| 62 | 45 | 60 | 60 | 70 | 0 | 0 | 30 | 0 |
| 63 | 0 | 0 | 0 | 0 | 0 | 0 | 0 | 0 |
| 64 | 70 | 80 | 65 | 75 | 0 | 0 | 0 | 0 |
| 65 | 55 | 60 | 40 | 55 | 0 | 0 | 0 | 0 |
| 66 | 50 | 65 | 50 | 45 | 0 | 0 | 0 | 0 |
| 67 | 95 | 100 | 95 | 95 | 93 | 90 | 90 | 70 |
| 68 | 93 | 98 | 85 | 75 | 75 | 70 | 75 | 20 |
| 69 | 75 | 93 | 75 | 70 | 0 | 0 | 0 | 0 |
| 70 | 95 | 95 | 90 | 85 | 25 | 20 | 20 | 10 |
| 71 | 80 | 93 | 55 | 80 | 25 | 20 | 10 | 10 |
| 72 | 45 | 93 | 50 | 30 | 30 | 35 | 35 | 20 |
| 73 | 93 | 100 | 70 | 93 | 30 | 55 | 45 | 25 |
| 74 | N.T.* | N.T.* | — | — | — | — | — | — |
| 75 | 65 | 75 | 70 | 55 | 25 | 30 | 30 | 20 |
| 76 | 90 | 85 | 85 | 80 | 25 | 20 | 20 | 0 |

TABLE 2-continued

Post-Emergence Herbicidal Activity
Application Rate: 27.5 micrograms/cm², unless otherwise noted

| Compound No. | Broad-Leaf Plants % Phytotoxicity | | | | Grasses % Phytotoxicity | | | |
|---|---|---|---|---|---|---|---|---|
| | Lambsquarter | Mustard | Pigweed | Soybean | Crabgrass | Watergrass | Wild Oats | Rice |
| 77 | 85 | 100 | 90 | 75 | 25 | 20 | 20 | 20 |
| 78 | 90 | 98 | 85 | 75 | 20 | 20 | 20 | 0 |
| 79 | 90 | 60 | 80 | 93 | 60 | 70 | 70 | 25 |
| 80 | 0 | 20 | 0 | 20 | 0 | 0 | 0 | 0 |
| 81 | 70 | 98 | 85 | 80 | 35 | 65 | 65 | 25 |
| 82 | 20 | 25 | 35 | 30 | 0 | 0 | 0 | 0 |
| 83 | 75 | 100 | 75 | 85 | 35 | 20 | 55 | 0 |
| 84 | 60 | 30 | 45 | 40 | 63 | 55 | 40 | 30 |
| 85 | 75 | 40 | 45 | 90 | 45 | 45 | 35 | 0 |
| 86 | 40 | 65 | 35 | 30 | 0 | 0 | 0 | 0 |
| 87 | 90 | 90 | 90 | 90 | 65 | 70 | 70 | 25 |
| 88 | 80 | 65 | 55 | 85 | 20 | 20 | 10 | 10 |
| 89 | 85 | 98 | 90 | 88 | 0 | 65 | 90 | 0 |
| 90 | 85 | 70 | 50 | 83 | 55 | 65 | 70 | 30 |
| 91 | 83 | 98 | 85 | 75 | 25 | 60 | 78 | 10 |
| 92 | 0 | 0 | 0 | 0 | 0 | 0 | 0 | 0 |
| 93 | 70 | 80 | 65 | 80 | 30 | 35 | 25 | 0 |
| 94 | 25 | 20 | 20 | 20 | 0 | 0 | 0 | 0 |
| 95 | 65 | 65 | 65 | 40 | 25 | 20 | 0 | 0 |
| 96 | 65 | 70 | 70 | 55 | 0 | 0 | 0 | 0 |
| 97 | 70 | 80 | 65 | 55 | 0 | 0 | 0 | 0 |

N.T.* = Not Tested
<sup>a</sup>Tested at 15.6 micrograms/cm²

TABLE 2A

COMPARISON COMPOUNDS
Post-Emergence Herbicidal Activity
Application Rate: 27.5 micrograms/cm², unless otherwise noted

| Compound No. | Broad-Leaf Plants % Phytotoxicity | | | | Grasses % Phytotoxicity | | | |
|---|---|---|---|---|---|---|---|---|
| | Lambsquarter | Mustard | Pigweed | Soybean | Crabgrass | Watergrass | Wild Oats | Rice |
| C-1 | 20 | 20 | 0 | 25 | 0 | 0 | 0 | 0 |
| C-2 | 0 | 0 | 0 | 0 | 0 | 0 | 0 | 0 |
| C-3 | 0 | 0 | 0 | 0 | 0 | 0 | 0 | 0 |
| C-4 | 0 | 0 | 0 | 0 | 0 | 0 | 0 | 0 |
| C-5 | 0 | 0 | 0 | 0 | 0 | 0 | 0 | 0 |
| C-6 | 0 | 0 | 0 | 0 | 0 | 0 | 0 | 0 |
| C-7 | 0 | 0 | 0 | 0 | 0 | 0 | 0 | 0 |
| C-8 | 25 | 20 | 25 | 30 | 0 | 0 | 0 | 0 |
| C-9 | 20 | 20 | 10 | 25 | 0 | 0 | 0 | 0 |
| C-10 | 0 | 0 | 0 | 0 | 0 | 0 | 0 | 0 |
| C-11 | 20 | 0 | 0 | 20 | 0 | 0 | 0 | 0 |
| C-12 | 0 | 0 | 0 | 0 | 0 | 0 | 0 | 0 |
| C-13 | 0 | 0 | 0 | 0 | 0 | 0 | 0 | 0 |
| C-14 | 0 | 0 | 0 | 0 | 0 | 0 | 0 | 0 |
| C-15 | 25 | 25 | 0 | 30 | 25 | 10 | 45 | 45 |
| C-16 | 0 | 0 | 0 | 0 | 0 | 0 | 0 | 0 |

As can be seen from the above Table 1, the compounds of the invention generally exhibit a broad spectrum of excellent pre-emergence phytotoxic activity and especially so Compounds Nos. 2, 4, 7, 9, 12, 14, 16, 22. Moreover, as shown by Table 2 the compounds also generally exhibit post-emergence phytotoxic activity against broad-leaf plants and in some instances also against grasses, especially so Compound Nos. 7, 9, 12, 14, 16, 22 and 23. Also, it can be seen that the corresponding Comparison Compounds had much poorer activity than the corresponding compounds of the present invention.

Obviously, many modifications and variations of the invention described hereinabove and below can be made without departing from the essence and scope thereof.

What is claimed is:

1. A compound having the formula:

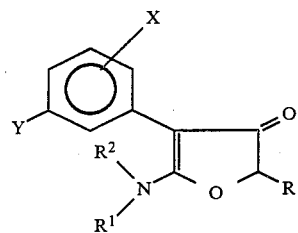

(I)

wherein R is lower alkyl, cycloalkyl having 3 through 7 carbon atoms; lower alkenyl; haloalkyl having 1 through 4 carbon atoms and 1 through 3 halo atoms independently selected from the group of fluoro, chloro, bromo or iodo; haloalkenyl having 2 through 4 carbon atoms and 1 through 3 halo atoms independently selected from the group of fluoro, chloro, bromo, or iodo; lower alkoxyalkyl wherein the alkyl and alkoxy moieties independently have 1 through 3 carbon atoms; alkylthioalkyl wherein the alkyl moieties independently have 1 through 3 carbon atoms; phenyl, naphth-1-yl; inden-1-yl; 4-fluorophenyl; arylalkylene having 1 through 3 carbon atoms in the alkylene moiety and wherein the aryl moiety is phenyl, naphth-1-yl or inden-1-yl; or R is a substituted aryl or substituted arylalkylene selected from the group having the formulas:

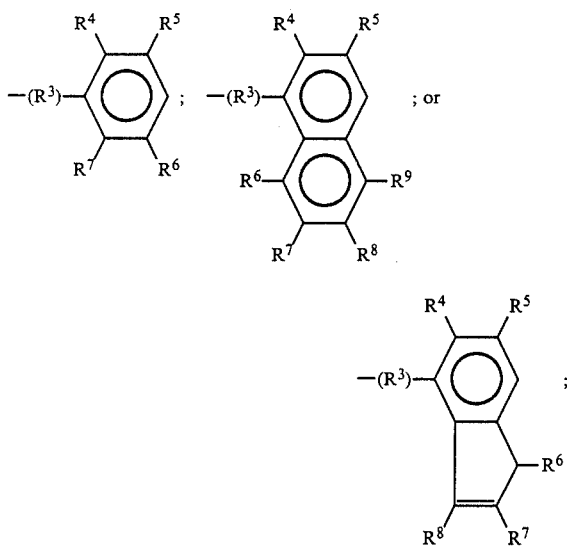

wherein one, two or three of $R^4$, $R^5$, $R^6$, $R^7$, $R^8$, and $R^9$ are independently selected from the group of lower alkyl, lower alkoxy, halo, nitro, or haloalkyl having 1 through 3 carbon atoms and 1 through 3 of the same or different halo atoms, and the remainder are hydrogen; and $R^3$ is a single bond or alkylene having 1 through 3 carbon atoms;

- $R^1$ is hydrogen or alkyl having 1 through 4 carbon atoms;
- $R^2$ is hydrogen, alkyl having 1 through 4 carbon atoms, alkenyl having 3 or 4 carbon atoms, lower alkoxycarbonylalkyl, lower alkoxyalkyl or lower alklylthioalkyl;
- $R^1$ and $R^2$ together with the nitrogen atom to which they are joined from a saturated or unsaturated nitrogen heterocycle having 4 through 6 ring atoms one of which is nitrogen and the remainder are carbon atoms;
- X is hydrogen, lower alkyl, lower alkoxy, halo, or trifluoromethyl and can be at any available position on the phenyl ring; and Y is lower alkyl, lower alkoxy, halo, lower haloalkyl having 1 through 4 carbon atoms and 1 through 3 of the same or different halo atoms, lower haloalkoxy having 1 through 4 carbon atoms and 1 through 3 of the same or different halo atoms, or lower haloalkylthio having 1 1 through 4 carbon atoms and 1 through 3 of the same or different halo atoms, with the proviso that when Y is other than trifluoromethyl and X is other than hydrogen, and $R^1$ and $R^2$ are each hydrogen than R is methyl, ethyl, propyl, 2-halophenyl, 2-lower alkylphenyl or 4-fluorophenyl; and compatible salts thereof.

2. The compound of claim 1 wherein one of $R^1$ or $R^2$ is hydrogen, methyl, ethyl or propyl.

3. The compound of claim 1 wherein one of $R^1$ or $R^2$ is methyl or ethyl and the other is hydrogen, methyl or ethyl.

4. The compound of claim 1 wherein one of $R^1$ or $R^2$ is hydrogen and the other is methyl, ethyl or propyl.

5. The compound of claim 1 wherein X is hydrogen.

6. The compound of claim 2 wherein X is hydrogen.

7. The compound of claim 3 wherein X is hydrogen.

8. The compound of claim 1 wherein R is phenyl, naphth-1-yl, 4-fluorophenyl or substituted aryl.

9. The compound of claim 8 wherein R is phenyl, naphthyl or a monosubstituted phenyl.

10. The compound of claim 9 wherein R is phenyl, halophenyl, or lower alkylphenyl.

11. The compound of claim 10 wherein R is phenyl, 4-fluorophenyl, 2-halophenyl, or 2-lower alkylphenyl.

12. The compound of claim 11 wherein X is hydrogen and $R^1$ and $R^2$ are independently selected from the group of hydrogen, methyl or ethyl.

13. The compound of claim 1 wherein R is lower alkyl, cycloalkyl, lower alkenyl, haloalkyl or haloalkenyl.

14. The compound of claim 13 wherein one of $R^1$ or $R^2$ is hydrogen, methyl or ethyl and the other is methyl or ethyl.

15. The compound of claim 14 wherein R is methyl, ethyl or propyl.

16. The compound of claim 15 wherein one of $R^1$ or $R^2$ is hydrogen and the other is methyl or ethyl.

17. The compound of claim 16 wherein X is hydrogen.

18. A compound having the formula:

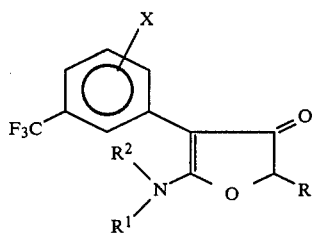

wherein R is lower alkyl, cycloalkyl having 3 through 7 carbon atoms; lower alkenyl; haloalkyl having 1 through 4 carbon atoms and 1 through 3 halo atoms independently selected from the group of fluoro, chloro, bromo or iodo; haloalkenyl having 2 through 4 carbon atoms and 1 through 3 halo atoms independently selected from the group of fluoro, chloro, bromo, or iodo; lower alkoxyalkyl wherein the alkyl and alkoxy moieties independently have 1 through 3 carbon atoms; lower alkylthioalkyl wherein the alkyl moieties independently have 1 through 3 carbon atoms; phenyl, naphth-1-yl, inden-1-yl; 4-fluorophenyl; arylalkylene having 1 through 3 carbon atoms in the alkylene moiety and wherein the aryl moiety is phenyl, naphth-1-yl or inden-1-yl; or R is a substituted aryl or substituted arylalkylene selected from the group having the formulas:

wherein one, two or three of $R^4$, $R^5$, $R^6$, $R^7$, $R^8$, and $R^9$ are independently selected from the group of lower alkyl, lower alkoxy, halo, nitro, or haloalkyl having 1 through 3 carbon atoms and 1 through 3 of the same or different halo atoms, and the remainder are hydrogen; and $R^3$ is a single bond or alkylene having 1 through 3 carbon atoms;

$R^1$ is hydrogen or alkyl having 1 through 4 carbon atoms;

$R^2$ is hydrogen, alkyl having 1 through 4 carbon atoms, alkenyl having 3 or 4 carbon atoms, lower alkoxycarbonylalkyl, lower alkoxyalkyl or lower alkylthioalkyl;

$R^1$ and $R^2$ together with the nitrogen atom to which they are joined form a saturated or unsaturated nitrogen heterocycle having 4 through 6 ring atoms one of which is nitrogen and the remainder are carbon atoms;

X is hydrogen, lower alkyl, lower alkoxy, halo, or trifluoromethyl and can be at any available position on the phenyl ring;

and compatible salts thereof.

19. The compound of claim 18 wherein $R^1$ and $R^2$ are independently hydrogen, methyl or ethyl.

20. The compound of claim 19 wherein one of $R^1$ or $R^2$ is methyl or ethyl and the other is hydrogen, methyl or ethyl.

21. The compound of claim 18 wherein one of $R^1$ or $R^2$ is methyl or ethyl and the other is hydrogen.

22. The compound of claim 19 wherein X is hydrogen and R is phenyl, naphthyl, 4-fluorophenyl, 2-halophenyl or 2-lower alkylphenyl.

23. The compound of claim 22 wherein one of $R^1$ or $R^2$ is hydrogen and the other is hydrogen methyl or ethyl.

24. The compound of claim 23 wherein R is phenyl, 2-fluorophenyl 2-chlorophenyl or 2-methylphenyl.

25. The compound of claim 23 wherein R is phenyl.

26. The compound of claim 23 wherein R is phenyl and one of $R^1$ or $R^2$ is hydrogen and the other is methyl.

27. The compound of claim 23 wherein R is phenyl and one of $R^1$ or $R^2$ is hydrogen and the other is ethyl.

28. The compound of claim 18 wherein R is lower alkyl, cycloalkyl, lower alkenyl, lower haloalkyl or lower haloalkenyl.

29. The compound of claim 28 wherein $R^1$ and $R^2$ are independently hyrogen, methyl or ethyl.

30. The compound of claim 29 wherein R is methyl, ethyl or propyl.

31. The compound of claim 30 wherein one of $R^1$ or $R^2$ is hydrogen and the other is methyl or ethyl and X is hydrogen.

32. The compound of claim 29 wherein X is hydrogen.

33. The compound of claim 18 wherein X is hydrogen.

34. The compound of claim 5 wherein Y is a lower haloalkyl having 1 or 2 carbon atoms.

35. A compound having the formula:

wherein Y is trifluoromethyl, chloro or bromo and wherein $R^1$ is hydrogen or methyl when Y is trifluoromethyl and $R^1$ is methyl or ethyl when Y is chloro or bromo.

36. A method for preparing the compound of claim 1 wherein R is phenyl, naphth-1-yl, inden-1-yl or a substituted aryl as defined in claim 1, which comprises the step of contacting the corresponding compound having the formula:

(A)

wherein X and Y are as defined in claim 1 and Z' corresponds to the desired R aryl or substituted aryl substituent, with a halogen selected from the group consisting of chlorine, bromine and iodine and water under reactive conditions thereby producing the corresponding compound of formula I.

37. The method of claim 36 wherein said method is conducted in an inert organic solvent at temperatures in the range of about from 0° to 100° C. and said halogen is bromine.

38. The method of claim 37 wherein liquid carboxylic acid is used as said inert organic solvent.

39. A herbicidal composition comprising a herbicidally effective amount of a compound according to claim 1, or mixtures of such compounds, and a compatible carrier.

40. A herbicidal composition comprising a herbicidally effective amount of a compound according to claim 18, or mixtures thereof, and a compatible carrier.

41. A herbicidal composition comprising a herbicidally effective amount of a compound according to claim 26, and a compatible carrier.

42. A herbicidal composition comprising a herbicidally effective amount of a compound according to 35, or mixtures of such compounds and a compatible carrier.

43. A method for preventing or destroying plants which comprises applying a herbicidally effective amount of a compound according to claim 1, or mixtures thereof, to the foliage or potential growth medium of said plants.

44. A method for preventing or destroying plants which comprises applying a herbicidally effective amount of a compound according to claim 18, or mixtures thereof, to the foliage or potential growth medium of said plants.

45. A method for preventing or destroying plants which comprises applying a herbicidally effective amount of a compound according to claim 26, to the foliage or potential growth medium of said plants.

46. A method for preventing or destroying plants which comprises applying a herbicidally effective amount of a compound according to claim 35, or mixtures thereof, to the foliage or potential growth medium of said plants.

47. A method for regulating the growth of plants which comprises applying to the foliage of said plants or their growth medium an amount of a compound according to claim 1, or mixtures thereof, effective to alter the growth pattern of such plants.

* * * * *